US006495518B1

(12) United States Patent
Hawiger et al.

(10) Patent No.: US 6,495,518 B1
(45) Date of Patent: Dec. 17, 2002

(54) METHOD FOR IMPORTING BIOLOGICALLY ACTIVE MOLECULES INTO CELLS

(75) Inventors: Jack J. Hawiger, Nashville, TN (US); Daniel Robinson, Lexington, KY (US); Ruth Ann Veach, Brentwood, TN (US); Xue Yan Liu, Nashville, TN (US); Danya Liu, Nashville, TN (US); Sheila Timmons, Nashville, TN (US); Robert D. Collins, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/450,071

(22) Filed: Nov. 29, 1999

Related U.S. Application Data

(63) Continuation-in-part of application No. 09/170,754, filed on Oct. 13, 1998, now Pat. No. 6,043,339, which is a division of application No. 09/052,784, filed on Mar. 31, 1998, which is a continuation of application No. 08/258,852, filed on Jun. 13, 1994, now Pat. No. 5,807,746.

(51) Int. Cl.$^7$ .............................................. A61K 38/16
(52) U.S. Cl. ............................................. 514/11; 514/9
(58) Field of Search ............................. 530/300; 514/1, 514/2, 23, 44, 9, 11

(56) References Cited

U.S. PATENT DOCUMENTS

| | | | | |
|---|---|---|---|---|
| 5,811,512 A | * | 9/1998 | Hirschmann et al. | 530/311 |
| 5,877,282 A | | 3/1999 | Nadler et al. | 530/350 |
| 5,916,872 A | | 6/1999 | Chang et al. | |
| 5,962,415 A | | 10/1999 | Nadler | 514/12 |
| 6,043,339 A | * | 3/2000 | Lin et al. | |

FOREIGN PATENT DOCUMENTS

| | | | |
|---|---|---|---|
| WO | WO98/11907 A1 | | 3/1998 |
| WO | wo-98/11907 | * | 3/1998 |

OTHER PUBLICATIONS

Verma et al (1997) Nature 389:239–242.*
Palù et al. (1999) J. Biotechnol. 68:1–13.*
Luo et al (2000) Nature Biotechnology 18:33–37.*
Fox, ASM News, Feb. 2000, 66 (2): 1–3.*
Donnelly et al. "DNA Vaccines", Annu. Rev. Immunol. 1997 15:617–48.*
Branch. "A good Antisense molecule is hard to find", TIBS Feb. 23, 1998 pp. 45–50.*
Anderson. "Human gene therapy", Nature vol. 392 1998 pp. 25–30.*
Qin et al. "Nuclear Factor kB contributes to excitotoxin-induced apoptosis in rat striatum" Mol. Pharmacology 53:33–42 (1998).

Friedler et al. "Backbone cyclic peptide, which mimics the nuclear localization signal of human immunodeficiency virus type 1 matrix protein, inhibits nuclear import and virus production in nondividing cells" *Biochemistry* 37:5616–5622 (1998).
Liu et al. "Identification of a functionally important sequence in the cytoplasmic tail of integrin Beta3 by using cell–permeable peptide analogs" *Proc. Natl. Acad. Sci. USA* 93:11819–11824 (1996).
Zhang et al "Preparation of functionally active cell–permeable peptides by single–step ligation of two peptide modules" *Proc. Natl. Acad. Sci. USA* 95:9184–9189 (Aug. 1998).
Delli–Bovi et al. "An Oncogene Isolated by Transfection of Kaposi's Sarcoma DNA Encodes a Growth Factor that is a Member of the FGF Family" Cell, 50:729–737, Aug., 1987.
Delli–Bovi et al. "Processing, Secretion, and Biological Properties of a Novel Growth Factor of the Fibroblast Growth Factor Family with Oncogenic Potential" Mol. Cell. Biol. 8(7):2933–2941, Jul., 1988.
Wolff et al. "Nuclear Protein Import: Specificity for Transport across the Nuclear Pore" Exp. Cell Res. 178:318–334, 1988.
Dang and Lee "Nuclear and Nucleolar Targeting Sequences of c–erb–A, c–myb, N–myc, p53, HSP70, and HIV tat Proteins" J. Biol. Chem. 264(30):18019–18023, Oct. 25, 1989.
Landford et al. "Comparison of Diverse Transport Signals in Synthetic Peptide–Induced Nuclear Transport" Exp. Cell Res. 186:32–38, 1990.
Kieran et al. "The DNA Binding Subunit of NF–kB is Identical to Factor KBF1 and Homologous to the rel Oncogene Product" Cell 62:1007–1018, Sep. 1990.
Nolan et al. "DNA Binding and IkB Inhibition of the Cloned p65 subunit of NF–kB, a rel–Related Polypeptide" Cell 64:961–969, Mar. 8,1991.
Stochaj and Silver "A Conserved Phosphoprotein that Specifically Binds Nuclear Localization Sequences is Involved in Nuclear Import" J. Cell Biol. 117(3):473–482, May, 1992.
Lentz et al. "The E1 Replication Protein of Bovine Papillomavirus Type 1 Contains an Extended Nuclear Localization Signal That Includes a p34cdc2 Phosphorylation Site" J. Virol. 67(3):1414–14231, Mar., 1993.

(List continued on next page.)

Primary Examiner—Remy Yucel
Assistant Examiner—Bronwen M. Loeb
(74) Attorney, Agent, or Firm—Needle & Rosenberg, P.C.

(57) ABSTRACT

The present invention relates to the delivery of biologically active molecules, such as peptides, nucleic acids and therapeutic agents, into the interior of cells by administering to the cells a complex comprising the molecule linked to an importation competent signal peptide. Such delivery can be utilized for purposes such as peptide therapy, gene transfer, and antisense therapy to regulate and/or eradicate systemic inflammatory response syndromes such as endotoxic shock.

1 Claim, 3 Drawing Sheets

OTHER PUBLICATIONS

Wessendorf et al. "Identification of a Nuclear Localization Sequence within the Structure of the Human Interleukin–1αPrecursor" J. Biol. Chem. 268(29):22100–22104, Oct. 15, 1993.

Friedman et al. "Mutagenesis of the Nuclear Localization Sequence in FGF–1 Alters Protein Stability but not Mitogenic Activity" Biochem & Biophy. Res. Comm. 198(3):1203–1208, Feb. 15, 1994.

Lin et al. "Inhibition of Nuclear Translocation of Transcription Factor NF–KB By a Synthetic Peptide Containing a Cell Membrane–permeable Motif and Nuclear Localization Sequence" J. of Biol. Chem. 270(24) 14255–14258, Jun. 16, 1995.

Rojas et al. "Controlling Epidermal Growth Factor (EGF-)–stimulated Ras Activation in Intact Cells by a Cell–permeable Peptide Mimicking Phosphorylated EGF Receptor" J. of Biol. Chem. 271:27456–27461, Nov. 1, 1996.

Torgerson et al. "Regulation of NF–kB, AP–1, NFAT, and STAT1 Nuclear Import in T Lymphocytes by Noninvasive Delivery of Peptide Carrying the Nuclear Localization Sequence of NF–kB p501" J. of Immunology 161:6084–6092, Dec. 1, 1998.

Hawiger, J. "Noninvasive Intracellular Delivery of Functional Peptides and Proteins" Curr. Opin. Chem. Biol. 3(1):89–94, Feb., 1999.

* cited by examiner

METHOD FOR IMPORTING BIOLOGICALLY ACTIVE MOLECULES INTO CELLS

This application is a continuation-in-part of, and claims benefit of priority to, U.S. Ser. No. 09/170,754, filed Oct. 13, 1998 (now U.S. Pat. No. 6,043,339), which is a divisional of U.S. Ser. No. 09/052,784, filed Mar. 31, 1998 (now abandoned), which is a continuation of U.S. Ser. No. 08/258,852, filed on Jun. 13, 1994 (now U.S. Pat. No. 5,807,746), all of which are herein incorporated by reference in their entirety.

This invention was made with partial government support under NIH Grant Nos. HL45994, HL62356, and DK54072. The United States government has certain rights in the invention.

BACKGROUND OF THE INVENTION

1. Field of the invention

The present invention relates to biologically active molecules and to methods for delivery of biologically active molecules into the interior of cells by administering to the cells a complex comprising the molecule linked to a signal peptide. The present invention also relates to the development of cell-permeable peptide analogs and to methods for the targeted delivery of these peptide analogs to control systemic inflammatory response syndromes such as endotoxic shock.

2. Background Art

Peptides have been developed for many therapeutic uses. For example, diseases currently targeted by new peptide drugs include heart conditions, cancers, endocrine disorders, neurological defects, respiratory conditions, allergies and autoimmune diseases. Although the manufacture of known therapeutic peptides can be achieved by known methods, i.e., classic synthetic techniques or recombinant genetic engineering, delivery of the peptides into a cell has remained problematic, since they cannot readily cross biological membranes to enter cells. Thus, current methods include permeabilization of the cell membrane, or microinjection into the cell. Both of these methods have serious drawbacks. Permeabilization of cells, e.g., by saponin, bacterial toxins, calcium phosphate, electroporation, etc., can only be practically useful for ex vivo methods, and these methods cause damage to the cells. Microinjection requires highly skilled technicians (thus limiting its use to a laboratory setting), it physically damages the cells, and it has only limited applications as it cannot be used to treat for example, a mass of cells or an entire tissue, because one cannot feasibly inject large numbers of cells.

Similarly, delivery of nucleic acids has been problematic. Methods currently employed include the permeabilization described above, with the above-described drawbacks, as well as vector-based delivery, such as with viral vectors, and liposome-mediated delivery. However, viral vectors can present additional risks to a patient, and liposome techniques have not achieved satisfactorily high levels of delivery into cells.

Signal peptide sequences,[1] which share the common motif of hydrophobicity, mediate translocation of most intracellular secretory proteins across mammalian endoplasmic reticulum (ER) and prokaryotic plasma membranes through the putative protein-conducting channels.[2-11] Alternative models for secretory protein transport also support a role for the signal sequence in targeting proteins to membranes.[12-15]

Several types of signal sequence-mediated inside-out membrane translocation pathways have been proposed. The major model implies that the proteins are transported across membranes through a hydrophilic protein conducting channel formed by a number of membrane proteins.[2-11] In eukaryotes, newly synthesized proteins in the cytoplasm are targeted to the ER membrane by signal sequences that are recognized generally by the signal recognition particle (SRP) and its ER membrane receptors. This targeting step is followed by the actual transfer of protein across the ER membrane and out of the cell through the putative protein-conducting channel (for recent reviews, see references 2–5). In bacteria, the transport of most proteins across the cytoplasmic membrane also requires a similar protein-conducting channel.[7-11] On the other hand, signal peptides can interact strongly with lipids, supporting the proposal that the transport of some secretory proteins across cellular membranes may occur directly through the lipid bilayer in the absence of any proteinaceous channels.[14-15]

Thus, though many attempts have been made to develop effective methods for importing biologically active molecules into cells, both in vivo and in vitro, none has proved to be entirely satisfactory.

SUMMARY OF THE INVENTION

The present invention provides a method for treating or preventing sepsis in a human subject, comprising delivering to the subject a compound comprising a nuclear localization sequence of NF-κB such that nuclear importation of NF-κB is inhibited.

The present invention further provides a method of importing a biologically active molecule into a cell in a subject comprising administering to the subject a complex comprising the molecule linked to an importation competent signal peptide, thereby importing the molecule into the cell of the subject.

Additionally, the instant invention provides a method of importing a biologically active molecule into the nucleus of a cell in a subject comprising administering to the subject a complex comprising the molecule linked to an importation competent signal peptide and a nuclear localization peptide, thereby importing the molecule into the nucleus of the cell of the subject.

The present invention also provides a complex comprising an importation competent signal peptide linked to a biologically active molecule selected from the group consisting of a nucleic acid, a carbohydrate, a lipid, a glycolipid and a therapeutic agent.

BRIEF DESCRIPTION OF THE DRAWINGS

FIG. 2B (animals treated with 5 injections of SM peptide); FIG. 2C (animals treated with 5 injections of SN50 peptide); and, FIG. 2D (animals treated with 7 injections of SN50 peptide).

FIG. 3A shows the survival rate where the control (saline) was used. FIG. 3B illustrates that rate where cSN50 peptide was administered at 0.7 mg×7. FIG. 3C shows the survival rate where cSN50 peptide was administered at 1.5 mg×7. FIG. 3D illustrates that rate where SM peptide was administered at 1.5 mg×7. FIG. 3E shows the survival rate where cSN50 peptide (1.5 mg) was administered 30 min after endotoxin followed by 0.7 mg injections at 90, 150, 210 min and 6, 12, and 24 hrs.

DESCRIPTION OF THE PREFERRED EMBODIMENT

Figure 1B:
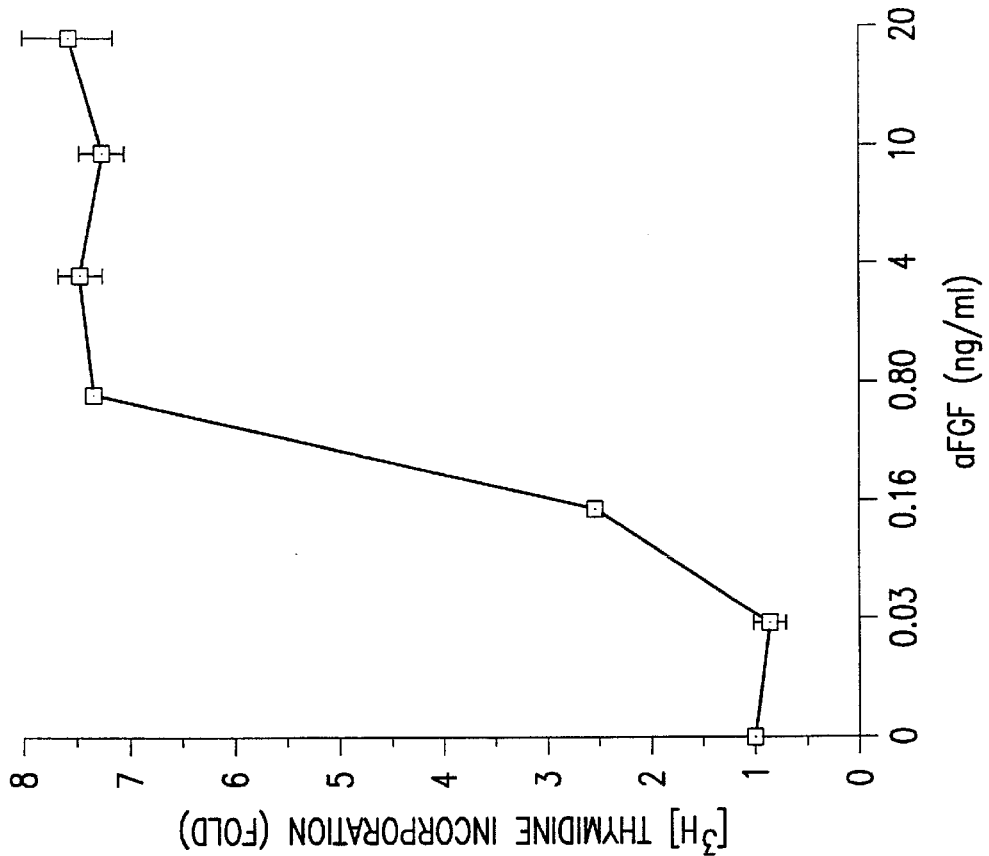
FIGS. 1A–1B are a graphic representation of [$^3$H] thymidine incorporation by NIH 3T3 cells stimulated with either (a) SA peptide, SAα peptide, ANL peptide or SM peptide or (b) acidic Fibroblast Growth Factor (aFGF).

The present invention may be understood more readily by reference to the following detailed description of specific embodiments and the Examples and Figures included therein.

The present invention provides the discovery that importing exogenous biologically active molecules into intact cells can be engineered by forming a complex by attaching an importation competent signal peptide sequence to a selected biologically active molecule and administering the complex to the cell. The complex is then imported across the cell membrane by the cell. Thus, the present invention provides a method of importing a biologically active molecule into a cell ex vivo or in vivo comprising administering to the cell, under import conditions, a complex comprising the molecule linked to an importation competent signal peptide, thereby importing the molecule into the cell.

As used herein, "biologically active molecule" includes any molecule which if imported into a cell, can have a biological effect. Naturally only those molecules which are of a size which can be imported into the cell are within the scope of the invention. However, since very large proteins (ranging from molecular weights of about 100,000 to around 1 million) are exported by cells (e.g., antibodies, fibrinogen, and macroglobulin), very large proteins can be imported into cells by this method. Therefore, size ranges for proteins from a few amino acids to around a thousand amino acids can be used. A preferable size range for proteins is from a few amino acids to about 250 amino acids. For any molecule, size ranges can be up to about a molecular weight of about 1 million, with a preferable size range being up to a molecular weight of about 25,000, and an even more preferable size range being up to a molecular weight of about 3,000. In addition, only those. molecules which can be linked to a signal peptide, either directly or indirectly, are within the scope of the invention. Likewise, the present invention requires that the complex is a administered under suitable conditions for effective import into the cell.

Examples of biologically active molecules include proteins, polypeptides and peptides, which include functional domains of biologically active molecules, such as growth factors, enzymes, transcription factors, toxins, antigenic peptides (as for vaccines), antibodies, and antibody fragments. Additional examples of biologically active molecules include nucleic acids, such as plasmids, coding DNA sequences, mRNAs and antisense RNA molecules, carbohydrates, lipids and glycolipids. Further examples of biologically active molecules include therapeutic agents, in particular those with a low cell membrane permeability. Some examples of these therapeutic agents include cancer drugs, such as Daunorubicin,[26] and toxic chemicals which, because of the lower dosage that can be administered by this method, can now be more safely administered.

A specific example of a biologically active molecule is the peptide comprising the nuclear location sequence (NLS) of acidic fibroblast growth factor (aFGF), listed herein as SEQ ID NO:2. As demonstrated in the examples below, the NLS of aFGF, when linked to a signal peptide and transported into cells (e.g., the entire peptide listed herein as SEQ ID NO:4), induces a mitogenic response in the cells. Another example of a biologically active molecule is the peptide comprising the NLS of transcription factor NF-κB subunit p50, listed herein as SEQ ID NO:10. As shown in the examples herein, when a peptide comprising the signal sequence of K-FGF and the NLS of transcription factor NF-κB p50 subunit, this peptide (called SN50) being listed herein as SEQ ID NO:9, is transfected into cells having transcription factor NF-κB, the normal translocation of active NF-κB complex into the nucleus is inhibited. In this manner, cell growth can be inhibited by inhibiting the action of NF-κB and therefore inhibiting the expression of genes controlled by transcription factor NF-κB.

Yet another example of a biologically active molecule is an antigenic peptide. Antigenic peptides can be administered to provide immunological protection when imported by cells involved in the immune response. Other examples include immunosuppressive peptides (e.g., peptides that block autoreactive T cells, which peptides are known in the art). Numerous other examples will be apparent to the skilled artisan.

Suitable import conditions are exemplified herein and include cell and complex temperature between about 180° C. and about 42° C., with a preferred temperature being between about 22° C. and about 37° C. For administration to a cell in a subject the complex, once in the subject, will of course adjust to the subject's body temperature. For ex vivo administration, the complex can be administered by any standard methods that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the complex can be added to, for example, a blood sample or a tissue sample from the patient or to a pharmaceutically acceptable carrier, e.g., saline and buffered saline, and administered by any of several means known in the art. Examples of administration include parenteral administration, e.g., by intravenous injection including regional perfusion. through a blood vessel supplying the tissues(s) or organ(s) having the target cell(s), or by inhalation of an aerosol, subcutaneous or intramuscular injection, topical administration such as to skin wounds and 1 lesions, direct transfection into, e.g., bone marrow cells prepared for transplantation and subsequent transplantation into the subject, and direct transfection into an organ that is subsequently transplanted into the subject. Further administration methods include oral administration, particularly when the complex is encapsulated, or rectal administration, particularly when the complex is in suppository form. A pharmaceutically acceptable carrier includes any material that is not biologically or otherwise undesirable, i.e., the material may be administered to an individual along with the selected complex without causing any undesirable biological effects or interacting in a deleterious manner with any of the other components of the pharmaceutical composition in which it is administered. Administration can be performed for a time length of about 1 minute to about 72 hours. Preferable time lengths are about 5 minutes to about 48 hours, and even more preferably about 5 minutes to about 20 hours, and even more preferably about 5 minutes to about 2 hours. Optimal time lengths and conditions for any specific complex and any specific target cell can readily be determined, given the teachings herein and knowledge in the art.[27] Specifically, if a particular cell type in vivo is to be targeted, for example, by regional perfusion of an organ or tumor, cells from the target tissue can be biopsied and optimal dosages for import of the complex into that tissue can be determined in vitro, as described herein and as known in the art, to optimize the in vivo dosage, including concentration and time length. Alternatively, culture cells of the same cell type can also be used to optimize the dosage for the target cells in vivo.

For either ex vivo or in vivo use, the complex can be administered at any effective concentration. An effective concentration is that amount that results in importation of the biologically active molecule into the cell. Such a concentration will typically be between about 0.5 nM to about 100 μM (culture medium concentration (ex vivo) or blood serum concentration (in vivo)). Optimal concentrations for a particular complex and/or a particular target cell can be readily determined following the teachings herein. Thus, in vivo dosages of the complex include those which will cause the blood serum concentration of the complex to be about 0.5 nM to about 100 μM. A preferable concentration is about 2 nM to about 50 μM. The amount of the complex administered will, of course, depend upon the subject being treated, the subject's age and weight, the manner of administration, and the judgment of the skilled administrator. The exact amount of the complex will further depend upon the general condition of the subject, the severity of the disease/condition being treated by the administration and the particular complex chosen. However, an appropriate amount can be determined by one of ordinary skill in the art using routine optimization given the teachings herein.

Parenteral administration, e.g., regional perfusion, if used, is generally characterized by injection. Injectables can be prepared in conventional forms, such as liquid solutions, suspensions, or emulsions. A slow release or sustained release system, such as disclosed in U.S. Pat. No. 3,710,795, can also be used, allowing the maintenance of a constant level of dosage.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein, and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the Eke. Actual methods of preparing such dosage forms are known, or will be apparent, to those skilled in this art; for example, see Remington's Pharmaceutical Sciences.[27]

The present invention utilizes a complex comprising the selected biologically active molecule linked to an importation competent signal peptide. As discussed above, the biologically active molecule can be selected from any of a variety of molecules, with its selection being dependent upon the purpose to be accomplished by importing the molecule into the selected cell. An "importation competent signal peptide," as used herein, is a sequence of amino acids generally of a length of about 10 to about 50 or more amino acid residues, many (typically about 55–60%) residues of which are hydrophobic such that they have a hydrophobic, lipid-soluble portion.[1] The hydrophobic portion is a common, major motif of the signal peptide, and it is often a central part of the signal peptide of protein secreted from cells. A signal peptide is a peptide capable of penetrating through the cell membrane to allow the export of cellular proteins. The signal peptides of this invention, as discovered herein, are also "importation competent," i.e., capable of penetrating through the cell membrane from outside the cell to the interior of the cell. The amino acid residues can be mutated and/or modified (i.e., to form mimetics) so long as the modifications do not affect the translocation-mediating function of the peptide. Thus the word "peptide" includes mimetics and the word "amino acid" includes modified amino acids, as used herein, unusual amino acids, and D-form amino acids. All importation competent signal peptides encompassed by this invention have the function of mediating translocation across a cell membrane from outside the cell to the interior of the cell. Such importation competent signal peptides could potentially be modified such that they lose the ability to export a protein but maintain the ability to import molecules into the cell. A putative signal peptide can easily be tested for this importation activity following the teachings provided herein, including testing for specificity for any selected cell type.

Signal peptides can be selected, for example, from the SIGPEP database, which also lists the origin of the signal peptide.[30,38] When a specific cell type is to be targeted, a signal peptide used by that cell type can be chosen. For example, signal peptides encoded by a particular oncogene can be selected for use in targeting cells in which the oncogene is expressed. Additionally, signal peptides endogenous to the cell type can be chosen for importing biologically active molecules into that cell type. And again, any selected signal peptide can be routinely tested for the ability to translocate across the cell membrane of any given cell type according to the teachings herein. Specifically, the signal peptide of choice can be conjugated to a biologically active molecule, e.g., a functional domain of a cellular protein or a reporter construct, and administered to a cell, and the cell is subsequently screened for the presence of the active molecule. The presence of modified amino acids in the signal peptide can additionally be useful for rendering a complex, wherein the biologically active molecule is a peptide, polypeptide or protein, more resistant to peptidase in the subject. Thus these signal peptides can allow for more effective treatment by allowing more peptides to reach their target and by prolonging the life of the peptide before it is degraded. Additionally, one can modify the amino acid sequence of the signal peptide to alter any proteolytic cleavage site present in the original signal sequence for removing the signal sequence. Clearage sites are characterized by small, positively charged amino acids with no side chains and are localized within about 1 to about 4 amino acids from the carboxy end of the signal peptide.[1]

An example of a useful signal peptide is the signal peptide from Capasso fibroblast growth factor (K-FGF),[6-17] listed herein as SEQ ID NO:5. Any signal peptide, however, capable of translocating across the cell membrane into the interior of the selected target cell can be used according to this invention.

By "linked" as used herein is meant that the biologically active molecule is associated with the signal peptide in such a manner that when the signal peptide crosses the cell membrane, the molecule is also imported across the cell membrane. Examples of such means of linking include (1) when the molecule is a peptide, the signal peptide (and a nuclear localization peptide, if desired) can be linked by a peptide bond, i.e., the two peptides can be synthesized contiguously; (2) when the molecule is a polypeptide or a protein (including antibody), the signal peptide (and a nuclear localization peptide, if desired). can be linked to the molecule by a peptide bond or by a non-peptide covalent bond (such as conjugating a signal peptide to a protein with a cross-linking reagent); (3) for molecules that have a negative charge, such as nucleic acids, the molecule. and the signal peptide (and a nuclear localization peptide, if desired) can be joined by charge-association between the negatively charged molecule and the positively-charged amino acids in the peptide or by other types of association between nucleic acids and amino acids; (4) chemical ligation methods can be employed to create a covalent bond between the carboxy-terminal amino acid of the signal peptide (and a nuclear localization peptide, if desired) and the molecule. Methods (1) and (2) are typically preferred.

Examples of method (1) are shown below wherein a peptide is synthesized, by standard means known in the art,[24,25] that contains, in linear order from the amino-terminal end, a signal peptide sequence, an optional spacer amino acid region, and a biologically active amino acid sequence. Such a peptide could also be produced through recombinant DNA techniques, expressed from a recombinant construct encoding the above-described amino 10 acids to create the peptide.[28]

For method (2), either a peptide bond, as above, can be utilized or a non-peptide covalent bond can be used to link the signal peptide with the biologically active polypeptide or protein. This non-peptide covalent bond can be formed by methods standard in the art, such as by conjugating the signal peptide to the polypeptide or protein via a cross-linking reagent, for example, glutaraldehyde. Such methods are standard in the art.[29] For method (3) the molecules can simply be mixed with the signal peptide and thus allowed to associate. These methods are performed in the same manner as association of nucleic acids with cationic liposomes.[32-34] Alternatively, covalent (thioester) bonds can be formed between nucleic acids and peptides. Such methods are standard in the art.

For method (4), standard chemical ligation methods, such as using chemical cross-linkers interacting with the carboxy-terminal amino acid of the signal peptide, can be utilized. Such methods are standard in the art (see, e.g., Goodfriend,[31] which uses water-soluble carbodiimide as a ligating reagent) and can readily be performed to link the carboxy terminal end of the signal peptide to any selected biologically active molecule.

The complex that is administered to a subject can further comprise a liposome. Cationic and anionic liposomes are contemplated by this invention, as well as liposomes having neutral lipids. Cationic liposomes can be complexed with the signal peptide and a negatively-charged biologically active molecule by mixing these components and allowing them to charge-associate. Cationic liposomes are particularly useful when the biologically active molecule is a nucleic acid because of the nucleic acid's negative charge. Examples of cationic liposomes include lipofectin, lipofectamine, lipofectace and DOTAP.[32-34] Anionic liposomes generally are utilized to encase within the liposome the substances to be delivered to the cell. Procedures for forming cationic liposomes encasing substances are standard in the art[35] and can readily be utilized herein by one of ordinary skill in the art to encase the complex of this invention.

Any selected cell into which import of a biologically active molecule would be useful can be targeted by this method, as long as there is a means to bring the complex in contact with the selected cell. Cells can be within a tissue or organ, for example, supplied by a blood vessel into which the complex is administered. Additionally, the cell can be targeted by, for example, inhalation of the molecule linked to the peptide to target the lung epithelium. Some examples of cells that can be targeted by this inventive method include fibroblasts, epithelial cells, endothelial cells, blood cells and tumor cells, among many. In addition, the complex can be administered directly to a tissue site in the body. As discussed above, the signal peptide utilized can be chosen from signal peptides known to be utilized by the selected target cell, or a desired signal peptide can be tested for importing ability given the teachings herein. Generally, however, all signal peptides have the common ability to cross cell membranes due, at least in part, to their hydrophobic character. Thus, in general, a membrane-permeable signal peptide can be designed and used for any cell type, since all eukaryotic cell membranes have a similar lipid bilayer.

One particularly useful example is to import an antigenic peptide into cells of the immune system, thereby allowing the antigen to be presented by antigen-presenting cells, and an immune response to the antigen to be developed by the subject. These antigenic peptide-containing complexes can be administered to the subject according to standard methods of administering vaccines, e.g., intramuscularly, subcutaneously or orally, and effectiveness can be measured by subsequent measuring of the presence of antibodies to the antigen. The present invention also provides a method of importing a biologically active molecule into the nucleus of a cell in a subject comprising administering to the subject a complex comprising the molecule linked to an importation competent signal peptide and a nuclear localization peptide, thereby importing the molecule into the nucleus of the cell of the subject. A nuclear localization peptide, as used herein, is a peptide having the function of delivering an intracellular peptide into the nucleus of the cell. Such nuclear localization sequences are known in the art to have this function[36,37]. An example of a nuclear localization peptide is the nuclear localization sequence of aFGF, listed herein as SEQ ID NO:2. An example of a signal peptide (K-FGF) linked to a nuclear localization peptide (aFGF) is set forth in SEQ ID NO:3. As these examples demonstrate, the nuclear localization peptide sequences can be synthesized as a peptide contiguous with the signal peptide, if desired. Additionally, separate peptides can be linked by any means such as described herein.

The present invention provides a method for treating or preventing sepsis in a human subject, comprising delivering to the subject a compound comprising a nuclear localization sequence of NF-κB such that nuclear importation of NF-κB is inhibited in a presently preferred embodiment, one or all of AP-1, NFAT and STAT-1 are also inhibited.

In one embodiment exemplified below, the nuclear localization sequence of NF-κB is delivered into the cells of the subject by linkage to an importation competent signal peptide (signal sequence). See also, Rojas, M. et al., 1998 Nature Biotechnology 16:370–375. However, the nuclear localization sequence of NF-κB could also be delivered by other means such as by physical methods of introducing proteins into cells (microinjection, electroporation, biolistics); chemical or biological pore formation (digitonin, pore forming proteins and ATP treatment); use of modified proteins (lipidated proteins and bioconjugates, such as with an immunotoxin); and, particle uptake (microspheres, virus mimics, induced pinocytosis). Patton, J., 1998 Nature Biotechnology 16:141–143; Putney and Burke, 1998 Nature Biotechnology 16:153–157 and Fernandez and Bayley, 1998 Nature Biotechnology 16:418–420.

Alternatively, one could deliver the nuclear localization sequence of NF-κB by administering to the subject a nucleic acid encoding a nuclear localization sequence of NF-κB. Such a nucleic acid could be delivery for example as naked DNA, with a viral vector, or by means such as cationic liposomes.

The present invention also provides a method of importing a biologically active molecule into the nucleus of a cell in a subject comprising administering to the subject a complex comprising the molecule linked to an importation competent signal peptide and a nuclear localization peptide, thereby importing the molecule into the nucleus of the cell of the subject.

The present invention also provides a method of regulating growth of a cell in a subject comprising administering to the subject a complex comprising a growth regulatory peptide linked to an importation competent signal peptide to import the growth regulatory peptide into the cell of the subject thereby regulating the growth of the cell. Growth can be stimulated or inhibited depending upon the growth regulatory peptide selected. It is to be noted that the present invention provides regulation of cell growth also by administering a nucleic acid encoding a growth regulatory peptide under functional control of a suitable promoter for expression in a specific target cell, wherein the nucleic acid is complexed with a signal peptide and administered to the target cell.

There are numerous growth regulatory peptides known in the art, any of which can be utilized in this invention, if appropriate for the target cell type and the type of regulation desired. The signal peptide facilitates the efficient import of the growth regulatory peptide into the target cell and, once the regulatory peptide is imported, it functions to regulate cell growth in its specific manner. A particularly useful target cell is a tumor cell in which the method can be used to inhibit further aberrant cell growth. Cell growth can be stimulated by administering a growth regulatory peptide comprising the nuclear localization sequence of acidic fibroblast growth factor (aFGF). Cell growth can be inhibited by administering peptides that inhibit growth, for example peptides that inhibit transcription in the cell, such as the NLS of the p50 subunit of transcription factor NF-κB.

An example of this method is seen below in the examples wherein the growth regulatory peptide stimulates cell growth and comprises the nuclear localization signal of aFGF. As this example demonstrates, the growth regulatory peptide, if desired, can be synthesized contiguously with the signal peptide, though any known method can be utilized to link them. An example of a contiguous peptide is set forth in SEQ ID NO:3 and SEQ ID NO:4. Another example is provided below, wherein a complex (listed as SEQ ID NO:9) comprising the membrane-permeable signal peptide of K-FGF linked to the NLS of transcription factor NF-κB p50 subunit is administered and inhibits the expression of genes encoding pro-inflammatory mediators.

The invention also provides a method of inhibiting expression in a cell in a subject of a gene controlled by transcription factor NF-κB comprising administering to the subject a complex comprising an importation competent signal peptide linked to a nuclear localization peptide of an active subunit of NF-κB complex. Many genes controlled by NF-κB are known in the art, and others can be readily tested by standard means. Examples of such genes include cytokines and interleukins, such as IL-1, IL-6, granular colony stimulating factor, plasminogen activator inhibitor and pro-coagulant tissue factor. Additionally, organisms having genes affected by NF-κB can be inhibited by this method, such organisms including human immunodeficiency virus (HIV) and cytomegalovirus (CMV). The optimal inhibitory peptide for specific cell types and specific genes can readily be determined by standard methods given the teachings herein. Additionally, the optimal inhibitory peptide for a specific cell type subjected to a specific stimulant can readily be determined.

An example is provided herein wherein translocation of the NF-κB complex to the nucleus in endothelial cells stimulated with lipopolysaccharide,(LPS) is inhibited by a complex comprising a signal peptide linked, to the NLS of subunit p50 of NF-κB. Presumably, the NLS of subunit p50 interferes with translocation of the complex to the nucleus due to competitive binding. Any cell type subjected to any (or no) stimulus can be readily screened for the optimal inhibitory peptide, i.e., the optimal NLS of a subunit of NF-κB, for that cell type. For example, for LEII cells, as demonstrated herein, the NLS of p50 is optimal.

The subunits of NF-κB complex are known in the art.[43] They include p50, p65 and cellular REL (c-REL). The nuclear localization sequences of these subunits are also known. An "active" subunit of NF-κB complex, as used herein, means a subunit which, when it is inhibited, causes transcription factor NF-κB not to function to mediate transcription of genes under its control. The nuclear location peptide used in this method can be a modification of the known NLS of these subunits are long as it retains the function of inhibiting expression of a gene controlled by NF-κB, as can be readily determined according to the teachings herein and knowledge in the art.

The invention further provides a method of stimulating the immune system of a subject comprising administering to the subject a complex comprising an importation competent signal peptide linked to an antigenic peptide. The complex can be administered to the subject by standard means known in the art for administering vaccines. The method can facilitate uptake of the antigen into cells for subsequent antigen presentation and the resultant known cascade of the immune system to result in the stimulation of immunity to the antigen.

Furthermore, if known peptides for blocking auto-reactive T cells are linked to a signal peptide and administered to a subject, an immuno-suppressive effect can be stimulated in the subject. Such a method of stimulating immuno-suppression can be used to treat autoimmune diseases such as multiple sclerosis. These blocking peptides can also be administered by known methods for administering peptides, such as methods for administering vaccines.

The invention also provides a complex comprising a biologically active molecule linked to an importation competent signal peptide and to a nuclear localization peptide. The linkage can be made as described above or otherwise known in the art. Though, as described above, any signal peptide and any nuclear localization sequence can be utilized, such a complex is exemplified by the amino acid sequences set forth in SEQ ID NO:3 and SEQ ID NO:4, which contain the K-FGF signal peptide (SEQ ID NO:5) linked to the aFGF nuclear localization peptide (SEQ ID NO:2).

The invention further provides a complex comprising an importation competent signal peptide linked to biologically active molecule selected from the group consisting of a nucleic acid, a carbohydrate, a lipid, a glycolipid and a therapeutic agent. This complex can further comprise a liposome. These complexes can be formed as described above. Liposomes can be selected as described above. The complex can be placed in a pharmaceutically acceptable carrier.

As used herein, "a" can mean one or more, depending on the context in which it is used.

The invention is more particularly described in the following examples which are intended as illustrative only since numerous modifications and variations therein will be apparent to those skilled in the art.

Statement Concerning Utility

The present method, which provides an effective method for importing biologically active molecules into cells, has many uses, both in vivo and ex vivo. Specific utilities using the method are apparent and are exemplified as follows. In vivo, the method can be used to deliver into cells therapeutic molecules, such as peptides and proteins to regulate aberrant functions or to supply deficient cells; DNA for gene therapy (e.g., to provide the CFTR gene in cystic fibrosis patients); RNA for antisense therapy (e.g., to inhibit growth as in inhibiting expression in cancer cells); and therapeutic agents such as cancer drugs or toxic chemicals (which can be administered in lower dosages with this method as compared to previous methods not utilizing a signal peptide to more efficiently enter the cells). Ex vivo, the method allows efficient transfection of cells without performing cell-damaging procedures. Therefore, this method is useful ex vivo in any method that utilizes transfection, such as transecting reporter genes into cells to screen for compounds that affect expression of the reporter gene, and for transfecting bone marrow cells, blood cells, cells of an organ for subsequent transplantation into a subject or culture cells, with a gene to effect protein expression in the cells.

More specifically, this method can be used for anti-thrombotic therapy by administering functional domains of known cell receptors which mediate aggregation of platelets, by competitive binding. Additionally, the method can be used for immunosuppression in autoimmune diseases by introducing immunosuppressive peptides into cells involved in the immune response. Furthermore, growth inhibitors can be administered by this method to tumor cells to treat, for example, cancer cells.

This method can also be used to facilitate the absorption of biologically active molecules from, e.g., the mouth, stomach or intestinal tract by facilitating movement of the molecules into the connective tissue beneath the lining of the digestive tract. Also, by allowing one to design signal peptides with modified amino acids, one can stabilize biologically active peptides by making them more resistant to peptidases and therefore also prolong the action of the peptide.

In addition, methods of treating sepsis are also provided.

EXAMPLE I

The peptides used herein were synthesized by a step-wise solid-phase peptide synthesis approach[24] and purified by high performance liquid chromatography using $C_{18}$ reverse phase column as described.[25] The exact molecular weights of the purified peptides were confirmed by mass spectrometry analysis.

Amino acid residues 1–16 of the SM peptide were patterned after the predicted signal peptide sequence of K-FGF[16,17] (listed separately herein as SEQ ID NO:5), residues 17–19 were designed as a spacer, and residues 20–26 contain an epitope tag recognized by antibody (see SEQ ID NO:1). Amino acid residues 1–19 of the SA peptide are identical to those of the SM peptide. However, its carboxyl terminal residues 20–26 are same as the sequence of the ANL peptide (SEQ ID NO:2), which is derived from the nuclear localization sequence of acidic FGF.[18] The SA peptide is listed as SEQ ID NO:3. The amino acid sequence of the SAα peptide was the same as that of the SA peptide except it had a two amino acid residue extension (Met-Pro) at the carboxyl terminus, which created an epitope (Leu-Met-Pro) for anti-SM peptide antibody. The SAα peptide is listed herein as SEQ ID NO:4.

Membrane-Permeable Signal Sequence Peptide (SM Peptide)

A 26-residue peptide (referred to as SM, listed herein as SEQ ID NO: 1) that contained the predicted signal sequence of Kaposi fibroblast growth factor[16-17] (K-FGF) was chemically synthesized. An indirect immunofluorescence assay using antibody against epitope tag-containing SM peptide was employed to follow translocation of the SM peptide to the intracellular compartments of NIH 3T3 cells. A polyclonal anti-SM peptide antibody against the SM peptide-keyhole limpet haemocyanin conjugate (Pierce) was raised in rabbits and reacted with SM peptide in ELISA (titer>1:30,000). The intracellular SM peptide was detected by an indirect immunofluorescence assay using affinity-purified anti-SM peptide IgG and rhodamine-labeled anti-rabbit antibody (Kirkegaard & Perry). Briefly, confluent NIH 373 cells on the chamber slides (Nunc) were treated with either 0.5 ml SM peptide solution (100 $\mu$g ml$^{-1}$) in DMEM containing 10% FBS or with 0.5 ml DMEM containing 10% FBS only for 30 minutes at 37° C. The cells were fixed with 3.5% paraformaldehyde solution in PBS followed by 0.25%Triton X-100 in PBS and then treated with 1:20 anti-SM peptide IgG in PBS containing 0.5% bovine serum albumin (BSA) for 1.5 h. The intracellular SM peptide-antibody complexes were visualized by subsequent incubation with a rhodamine-labeled anti-rabbit polyclonal antibody for 1 h. In control systems, anti-SM peptide antibody was preabsorbed with the SM peptide. Intracellular localization of the SAα peptide was detected by immunofluorescence assay using affinity-purified anti-SM peptide IgG as described above for SM peptide. Following incubation of cells with SM peptide, intracellular deposits were observed in almost all cells. A ten-step z-position sectional scanning of the SM peptide-treated cells by the confocal laser scanning microscopy (CLSM) affirmed that these deposits were intracellular. Immunodetection of the SM peptide was specific because cells incubated with the peptide-antibody complex showed no evidence of intracellular peptide. Likewise, cells not exposed to SM peptide or cells exposed to SM peptide followed by the secondary antibody alone were negative. If cells were fixed with paraformaldehyde before peptide treatment, the cellular import of SM peptide was prevented.

To determine the rate of SM peptide import across cell membranes, a kinetic experiment was carried out with the SM peptide-treated NIH 3T3 cells. NIH 3T3 cells were treated at 37° C. with 0.5 ml SM peptide at 100 μg mL$^{-1}$ in DMEM containing 10% FBS for 1, 5, 15, 30, 60 and 120 minutes. Intracellular SM peptide deposits were detected by indirect immunofluorescence assay as described above. The intracellular staining of intracellular SM peptide was observed during the first 5 minute interval and plateaued at about 30 minutes, indicating that the signal sequence-mediated peptide import into cells is rapid. The 30-minute time point was therefore selected to determine the optimal peptide concentrations for detectable import.

To determine the optimal peptide concentration, NH 3T3 cells were treated for 30 minutes at 37° C. with 0.5 ml SM peptide solution in DMEM containing 10% FBS at the following concentrations: 0, 2, 10, 50, 100, and 150 μg ml$^{-1}$. Intracellular localization of the SM peptide was detected by indirect immunofluorescence assay as described above. Indirect immunofluorescence assay demonstrated detectable peptide in the form of intracellular punctate deposits when the cells were exposed to 2 μg/ml (about 800 nM) of peptide. The cellular import was concentration-dependent and reached a plateau between 50 μg/ml and 100 μg/ml.

Transport of the SM peptide across the cell membrane was temperature-dependent. No immunofluorescence staining was observed when the cells were treated for 30 minutes with 100 μg/ml of the peptide at 4° C., whereas, cells treated at either 22° C. or 37° C. showed numerous punctate deposits. Accordingly, cellular import of the SM peptide resumed when the incubation temperature shifted from 4° C. to 37° C.

Moreover, this signal sequence-mediated import is not limited to NIH 3T3 cells. The intracellular localization of SM peptide has been used in baby hamster kidney-21 cells, human umbilical vein endothelial cells (HUVF-Cs) and rodent endothelial cell line (LE-II), by the above indirect immunofluorescence assay, with the same results as with NIH 3T3 cells.

Membrane-Permeable Signal Peptide (SKP Peptide)

Intracellular localization of the membrane-permeable peptide was also shown by treatment of cells with proteases following peptide import. For this experiment, 41-residue peptide (referred to as SEP and listed herein as SEQ ID NO:6) that contained the same hydrophobic sequence as SM peptide followed by the sequence of K-FGF(129–153) was designed and synthesized. The latter was present in KP peptide not containing hydrophobic sequence that served as the control for the membrane-permeable SKP peptide. Both peptides possess tyrosine residues, therefore they were radiolabeled with $^{125}$I and examined for their ability to translocate into intact NIH 3T3 cells, as described below. Substantial radioactivity was detected in the $^{125}$I-SKP peptide-treated cells but not in $^{125}$I-SKP peptide-treated cells, indicating that the import of SKP peptide into cells was selectively achieved due to the presence of hydrophobic, membrane-permeable sequence. The intracellular $^{125}$I-SKP peptide was resistant to the action of proteases. After treatment of cells containing 125 I-SKP peptide with pronase or trypsin, no significant loss of cell-associated radioactivity was observed, suggesting that the $^{125}$I-SKP peptide was located in intracellular compartments (Table 1). The import of membrane-permeable peptide was not dependent on ATP as high energy source because cells depleted of about 95% of ATP showed a similar $^{125}$I-SKP peptide uptake as compared to ATP-positive cells (Table 1).

Both SKP and KP peptides were radiolabeled with $^{125}$I by the Iodogen method (Pierce). The specific activities of both peptides were similar (2.5×10$^4$ cpm/ng). NIH 3T3 cells were subcultured on a 60-mm dish and incubated at 37° C. for 3 days. The confluent monolayers (1.6×10$^6$ cells) on each dish were then washed twice with PBS and treated with 15 ng of $^{125}$I SKP or $^{125}$I-KP peptide at 37° C., for the indicated time. The cells were washed eight times with PBS and twice with 2 M NaCl buffer (pH 7.5) until no radioactivity could be detected in the washings. The washed cells were lysed in lysis buffer (10 mM Tris-HCl, pH 7.0, 0.1 mM EDTA, 1 mM phenylmethylsulphony fluoride, 1 mM dithiothreitol, and 1% Triton X-100) and the radioactivity in the cell lysates was counted in a Packard auto-gamma counter. In some experiments, the washed cells were further treated with pronase (1 mg/ml) or trypsin (0.05%) solution in DMEM for 5 min at 37° C. The supernatants and cells were separated and their radioactivities were counted separately. For ATP depletion assay, cells were incubated with 5 μg/ml antimycin, 6.5 mM 2-deoxyglucose, and 10 mM glucono-δ-lactone in DMEM for 2 h at 37° C. before addition of $^{125}$I-SKP peptide. The levels of ATP in ATP-depleted cells and normal cells were determined by ATP bioluminescent assay kit (Sigma). No measurable ATP was observed in ATP-depleted cells.

TABLE 1

IMPORT OF 12SI-SKP PEPTIDE INTO ATP-DEPLETED NIH 3T3 CELLS AND EFFECT OF PROTEASES ON CELL-ASSOCIATED $^{125}$I-SKP PEPTIDE

| ATP Depletion | Counts in cells (cpm/1.6 X-10' cells) | |
| --- | --- | --- |
| Untreated cells | 20,189 ± 2,109 | |
| APT-depleted cells | 22,266 ± 3,602 | |

| Protease Treatment | Counts in cell lysates | Counts in supernatants |
| --- | --- | --- |
| Untreated cells | 21,323 ± 853 | 2,966 ± 838 |
| Pronase | 21,791 ± 1,953 | 1,979 ± 75 |
| Trypsin | 23,193 ± 310 | 655 ± 70 |

For ATP depletion assay, confluent NIH 3T3 cells (1.6× 10$^6$ cells) in each dish were treated with or without ATP depleting reagents (antimycin, 2deoxyglucose, and glucono-δ-lactone) for 2 h at 37° C. Cells were then treated with 15 ng of $^{125}$I-SKP peptide for 30 min at 37° C. After complete removal of extracellular $^{125}$I-labeled peptides, the radioactivity in the cell lysates was counted. For the assay using proteases, cells were treated with $^{125}$I-SKP peptide and washed as described above. The $^{125}$I-SKF peptide-associated cells were then treated with pronase (1 mg/ml), trypsin (0.05%), or diluent for 5 min at 37° C. The radioactivities in the cell lysates and supernatants were counted separately. Data in Table 1 represent the mean the mean±SEM of triplicate determinations of a single experiment. The experiment was repeated three times with similar results.

Membrane-Permeable Signal Peptide with Functional Peptide Cargo (SA Peptide)

Having demonstrated the feasibility of the cellular import of signal sequence-containing peptides, functional cargo in the form of a sequence responsible for the nuclear localization of cellular proteins was linked to a signal peptide. The nuclear localization sequence (NLS) of acidic FGF (aFGF), because it has previously been reported to play an essential role in aFGF mitogenic activity, was utilized.[18] It had previously been shown that a mutant aFGF with deletion in its NLS region Asn-Tyr-Lys-Lys-Pro-Lys-Leu (NYKKPKL), listed herein as SEQ ID NO:2, failed to stimulate DNA synthesis and cell proliferation in vitro although it could still bind to the FGF receptor and induce intracellular receptor-mediated tyrosine phosphorylation and c-fos expression.[18] Additionally, a recent study[19] of nuclear transport of aFGF suggested that translocation of aFGF to the nucleus was necessary for stimulating DNA synthesis by aFGF in vitro.

A 26-residue hybrid peptide (referred to as SA, listed herein as SEQ ID NO:3) was designed and synthesized. It contains the signal sequence of K-FGF[16,17] at its amino terminal region (residues 1–16 of SEQ ID NO:3) and a "functional cargo" in the form of a nuclear localization sequence (NLS) of aFGF[18] at its carboxyl terminal region (residues 20–26 of SEQ ID NO:3), separated by a spacer region of Ala-Ala-Ala (residues 17–19 of SEQ ID NO:3). Thus, the SA peptide differs from the SM peptide only in its 7-residue carboxyl terminal "cargo" region. A functional assay was performed in which SA peptide was able to induce a mitogenic response of NIH 3T3 cells measured by [$^3$H] thymidine incorporation in a manner similar to aFGF bearing, the same NLS.[18]

In this functional assay, confluent 3T3 cells grown initially in DMEM containing 10% FBS were transferred to a low serum medium (DMEM containing 0.5% FBS) for 2 days. The test peptides, either SA peptide, SAα pep-tide, ANL peptide, or SM peptide, or aFGF, were added to a fresh low serum medium at the indicated concentrations at 37° C. After 16 hours, [$^3$H] thymidine was added and 4 hours later, the cells were washed with PBS, treated with trichloroacetic acid, solubilized with 0.15 M NaOH, and the radioactivity was determined in a liquid scintillation counter.

Figure 1A:
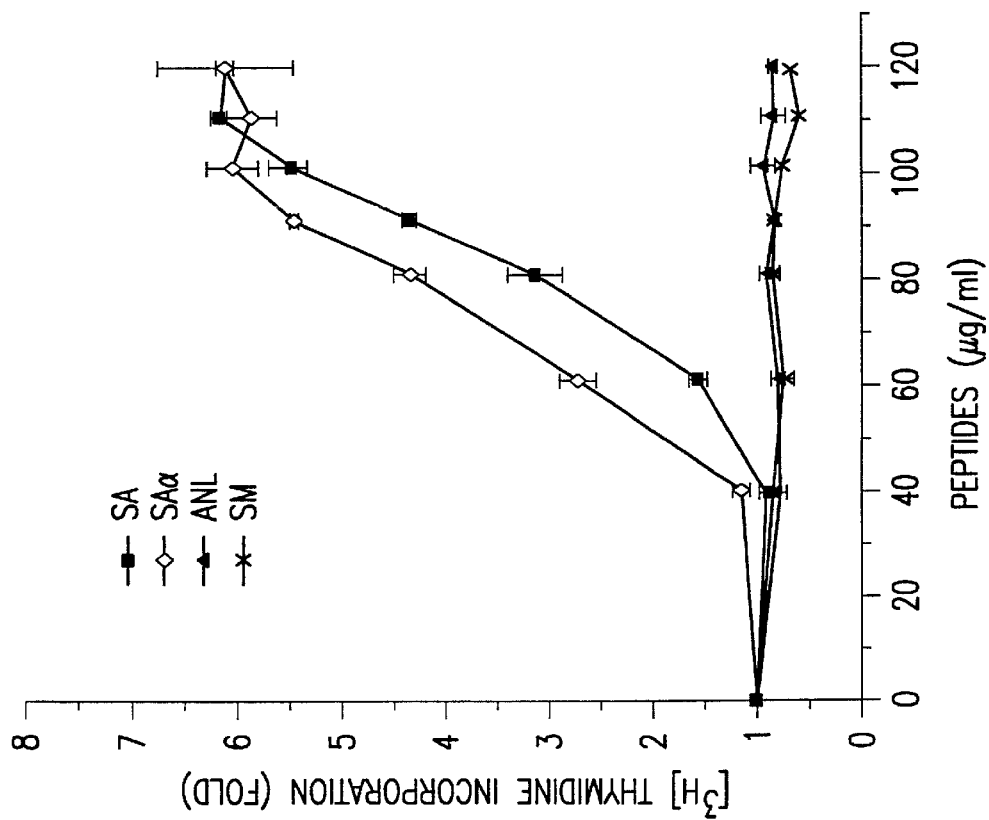

As shown in FIG. 1a, SA peptide stimulated [$^3$H] thymidine incorporation 6-fold, while aFGF induced approximately an 8-fold stimulation in the same assay (FIG. 1b). Bars represent the mean±S.E.M. of at least three independent experiments done in triplicate and calculated as multiplicity of counts in the tested sample over the control sample. SA peptide within the concentration range used (0 to 46 μM) was not cytotoxic as determined by staining with fluorescein diacetate/ethidium bromide.[20]

Mitogenic Activity of the SA Peptide

To determine whether the mitogenic activity of SA peptide required its full length sequence, two control peptides were examined in the same assay. They are the SM peptide containing signal peptide listed herein as SEQ ID NO:1) and a 7-residue peptide (referred to as ANL, listed herein as SEQ ID NO:2) representing the NLSof aFGF. Neither control peptide showed any significant mitogenic activity when tested within comparable concentration ranges (FIG. 1a). These results suggest that neither the signal sequence alone (SM peptide) nor the nuclear localization sequence alone (ANL peptide) was sufficient for mitogenesis. SA peptide therefore was effective in mitogenesis because it contained both the signal peptide sequence of K-FGF (for import into the cell) and nuclear localization sequence of aFGF (for mitogenic activity).

To further confirm the mitogenic activity of the SA peptide, its effect on DNA synthesis was examined. Serum-starved NIH 3T3 cells were treated with SA peptide, fixed, and the DNA concentration was determined by standard flow cytometric analysis. Specifically, confluent NIH 3T3 cells (1.3×10$^6$ cells) were serum-starved in DMEM containing 0.5% FBS for 2 days. The cells were untreated (control) or treated with SA peptide or aFGF for 20 h, harvested, spun down, and washed with serum-free PBS, three times. The cells were fixed with methanol precooled to −20° C. for DNA analysis carried out by the Flow Cytometry Research Service of Vanderbilt University. The data were the mean±S.E.M. of six measurements and were analyzed for statistical significance by analysis of variance.

As shown in Table 2, the DNA synthesis in the S-phase of the cell cycle was significantly increased when the cells were treated with the SA peptide at 100 μg/ml, which coincided with the active concentration in the thymidine incorporation assay (FIG. 1a). This result further confirms the role of the NLS region of aFGF in mitogenesis.[18] Thus, these data also are consistent with a recent demonstration using a genetic approach that schwannoma-derived growth factor requires NLS to exert its mitogenic activity.[21]

TABLE 2

DNA SYNTHESIS STIMULATED BY SA PEPTIDE AS COMPARED TO aFG1

| Stimulus | Diploid % S Phase |
| --- | --- |
| Control | 7.2 ± 0.7 |
| SA (50 μg ml$^{-1}$) | 6.7 ± 0.9 |
| SA (100 μg ml$^{-1}$) | 13.1 ± 0.5 (P < 0.05) |
| aFGF (15 ng ml$^{-1}$) | 27.8 ± 2.3 (P < 0.05) |

However, compared with aFGF, the SA peptide is less mitogenically potent in both thymidine incorporation and DNA analysis assays (FIG. 1 and Table 2). aFGF binds to the FGF receptors on NIH 3T3 cells and induces the tyrosine phosphorylation of a number of intracellular proteins that have been suggested as the FGF receptor signalling substrates.[22,23] In contrast, SA peptide did not stimulate the tyrosine phosphorylation of these intracellular proteins in the same cells even at the concentrations sufficient to induce DNA synthesis. Taken together, these results, make it unlikely that the mitogenic effect of SA peptide was mediated by FGF receptors.

Immunofluoresence Assay for Modified SA Peptide

The intracellular SA peptide could not be tracked by an immunofluorescence assay because it was not recognized by the available anti-SM peptide antibody. However, attaching two extra amino acid residues (Met-Pro) to the carboxyl terminus of the SA peptide produced a modified SA peptide (referred to as SAα, listed herein as SEQ ID NO:4) that contained a 3-amino acid epitope tag, Leu-Met-Pro, recognized by anti-SM peptide antibody in ELISA. Accordingly, intracellular SAα peptide was observed in a punctate staining pattern in the SAα-treated NIH 3T3 cells by an indirect immunofluorescence assay using anti-SM peptide antibody. Like SA peptide, SAα peptide was mitogenic in the thymidine incorporation assay. These results are consistent with the relationship between the SA peptides' import into the intracellular compartments and their mitogenic activity.

Membrane-Permeable Signal Peptide with Functional Peptide Cargo (SN50)

Having demonstrated the feasibility of the cellular import of membrane-permeable SM and SKP peptides, another functional cargo was attached to the amino-terminal hydrophobic sequence conferring membrane permeable capacity. For this purpose a sequence representing a functional domain of the nuclear factor κB (NF-κB) responsible for a nuclear localization signal was selected. Import of such a peptide into the cell would be measured by inhibition of nuclear translocation of NF-κB complex in stimulated cells. The NF-κB is a pleiotropic activator[39,40] that plays a critical role in the regulation of a number of cellular and viral genes, including the enhancer of human immunodeficiency virus (HIV). The inactive cytosolic form of NF-κB is a heterotrimer including p[50], p[65] and an inhibitory protein IκB.[41,42] Upon activation of cells with stimuli such as lipopolysaccharide (LPS) or cytokines,[43,44,45] IκB dissociates from the complex. This dissociation allows the translocation of heterodimer of p50 and p65 subunits to the nucleus. Both p50 and P65 subunits contain NLS, suggesting that the NLS sequence may be important for nuclear uptake of NF-κB.

To determine the functional significance of the NLS of p50 and p65 subunits, two peptides were designed and synthesized containing the sequence motifs. The first peptide (referred to as SN50, listed herein as SEQ ID NO:9) contained the signal sequence of K-FGF[16,17] at its amino-terminal region (residues 1–16) and a "functional cargo" in the form of NLS of NF-κB p50 subunit at its carboxy-terminal region (residues[17-26]). The second peptide is also a 26-residue peptide (referred to as SN65, listed herein as SEQ ID NO:8) that contains the same hydrophobic sequence and the NLS of p65 subunit. Both peptides were tested for their inhibitory effects on the nuclear translocation of the NF-κB complex in LE-II cells. Inducible $_κ$B binding activity was detectable by electrophoretic mobility shift assay in nuclear extracts from cells treated with LPS for 1 h.[43] However, this LPS-induced $_κ$B binding activity in nuclear fraction was reduced substantially in the SN50 peptide-treated cells. The inhibition by SN50 peptide was concentration-dependent, reading an 88% inhibition at 50 μg/ml. In contrast, no inhibition was observed in SN65 peptide-treated LEII cells. To exclude the possibility that the inhibition was caused by the interference of SN50 peptide in the binding of oligonucleotide probe to the NF-κB complex, SN50 peptide was incubated in vitro with nuclear extracts and radiolabeled probe. This maneuver was without any measurable effect on LPS-induced κB binding activity, suggesting that inhibition by SN50 peptide resulted from its action at the stage in which the active NF-κB complex moves from cytosol to nucleus. To determine whether the inhibition by SN50 peptide required a hydrophobic, membrane-permeable sequence, two control peptides (SM and N50 peptides, listed herein as SEQ ID NOS: 1 and 10, respectively) were also tested in the same mobility shift assay. N50 peptide contained the NLS without the hydrophobic sequence, whereas SM peptide contained a hydrophobic sequence without the NLS. Neither of these two peptides showed any significant effect on LPS-induced intracellular translocation of the NF-κB complex from the cytosol to the nucleus. These results suggest that neither the hydrophobic sequence alone (SM peptide) nor the nuclear localization sequence alone (N50 peptide) was sufficient for causing a functional inhibition of the NF-κB. Therefore, the observed inhibitory effect of SN50 must be attributed to its intracellular import which allowed the interaction of its intrinsic NLS with the nuclear membranes.

SN50 peptide contained the same epitope tag as SM peptide and thus could be recognized by the anti-SM peptide antibody in ELISA. This allowed direct affirmation by an indirect immunofluorescence assay that SN50 peptide was imported into LE-II cells to exert its functional role. Results showed that the intracellular SN50 peptide was distributed in a more nuclear staining pattern as compared to the intracellular SM peptide.

EXAMPLE II

The efficacy of the intracellular inhibition of nuclear import of NF-κB and other stress-responsive transactivators in abrogating in vivo changes resulting in lethal septic shock is based on the use of noninvasive intracellular delivery of the SN50 peptide containing a cell membrane-translocating sequence and NLS domain.[50-52] Two cell-permeable peptides, SM and SN50 were synthesized and purified as previously described,[51,52] and first tested in vitro in two types of cells known to be a target for LPS: murine macrophage J774 and endothelial LEII cell lines. (SM and SN50 peptides, listed herein as SEQ ID NOS: 1 and 9). The nuclear import of transcription factor NF-κB induced by septic shock inducer, LPS (10 ng/ml) in murine J774 macrophages was blocked by SN50 peptide but not by SM peptide (both at 31 μM). Whereas both peptides are cell permeable, the SM peptide functional domain contains "loss of function" mutated NLS sequence.[51,52] Similar pattern of results was obtained when J774 cells were stimulated with proinflammatory mediator of septic shock, TNF-α (20 U/ml). The SN50 peptide also inhibited inducible nuclear import of NF-κB in murine endothelial cells LEII stimulated with LPS (10 ng/ml) and TNFα (100 U/ml). Thus, the SN50 peptide but not the SM peptide caused intracellular inhibition of inducible nuclear import of NF-κB in murine macrophages and endothelial cells stimulated by LPS and TNFα.

Figure 2B:
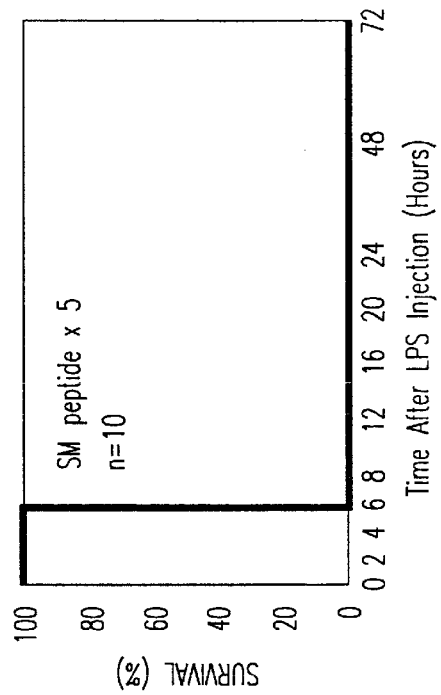
FIGS. 2A–2D demonstrate the improved survival of C57B1/6 mice treated with the SN50 peptide as compared to untreated or SM-peptide-treated controls. The groups of 5 mice each received intraperitoneal injections of D-galactosamine (20 mg in pyrogen-free saline) without or with peptide (2 mg) 30 min. before LPS from *E. coli* 0127:B8. The peptide injections were repeated at 30, 90, 150, and 210 minutes following LPS (as shown in FIGS. 2B and 2C); additional two injections were administered at 6 and 12 h following LPS (FIG. 2D). Surviving mice were euthanized after 72 h. Cumulative results of 2–3 groups are presented in FIG. 3A (control mice treated with 5 injection of saline (diluent))
Figure 2D:
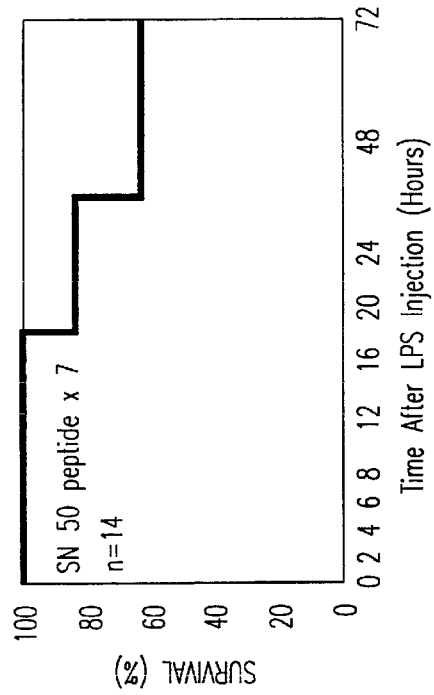
Figure 2A:
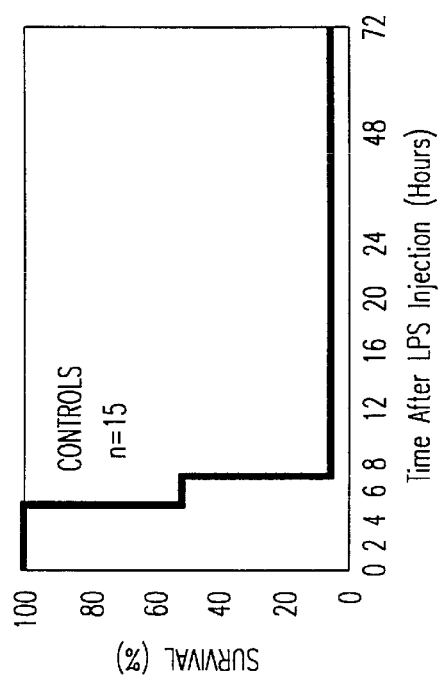
Figure 2C:
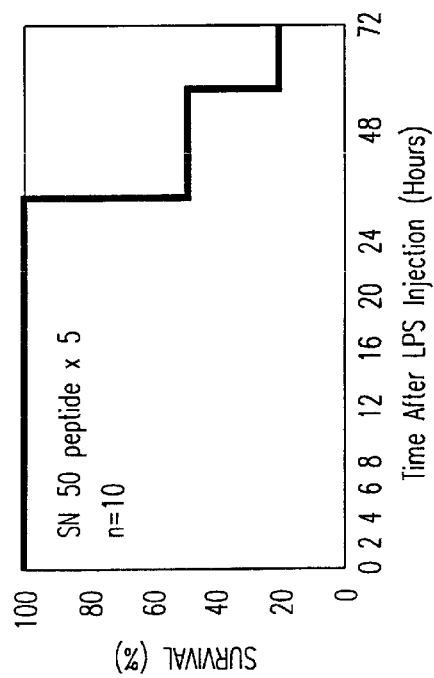

The efficacy of the SN50 peptide-directed inhibition of NF-κB and other stress-responsive transactivators in attenuating or preventing in vivo septic shock was demonstrated by injecting C57BL/6 mice intraperitoneally with D-galactosamine (20 mg) followed by LPS from E.coli serotype 0127:B8 (1 μg). Mice treated with D-galactosamine are sensitive to low doses of LPS.[60] As shown in FIG. 2A all but one mouse showed symptoms of acute illness within 4 hours and died within 6 hours following injection of LPS. In contrast, as shown in FIG. 2C, mice treated with the SN50 peptide (5 injections up to 3½ h after LPS) showed no symptoms of shock and survived the first 24 h. By 48 h, 50% mice survived and by 72 h 20% survival was observed. The protective in vivo effect is dependent on functional NLS domain of the SN50 peptide, because it was abrogated when SM peptide with mutated NLS domain was used. All SM peptide-treated mice (5 injections up to 3½ h after LPS) showed symptoms of acute illness and died within 5 h (FIG. 2B). The in vivo protective effect of SN50 peptide was time- and concentration-dependent. Administration of SN50 peptide extended to 6 and 12 h following LPS (7 intraperitoneal injections) resulted in 64% survival at 72 h (FIG. 2D). The differences in survival are statistically significant with P<0.001 based on the log rank test.[60]

As this model of septic shock is characterized by fulminant liver injury, histopathologic analysis focused on the liver. Sections obtained from mice receiving lethal combination of D-galactosamine and LPS revealed diffuse hepatocellular injury with hallmarks of apoptosis (fragmented nuclei), engorgement of blood vessels filled with platelet thrombi, and extravasation of red blood cells. Identical pattern of massive apoptosis of hepatocytes accompanied by hemorrhagic liver necrosis was observed in mice treated with SM peptide. In contrast, tissue sections from the liver of SN50 peptide-treated mice that survived septic shock for 72 h, displayed almost normal liver architecture without any overt signs of apoptosis of hepatocytes and hemorrhagic necrosis. The simplest implication of these results is that intraperitoneal administration of the SN50 peptide provides significant cytoprotection of the liver, a primary target organ in murine model of D-galactosamine/LPS-induced septic shock.[57,60]

These evidence that the SN50 peptide administered in vivo attenuates and/or prevents lethal septic shock induced by LPS. The microbial inducer of septic shock, LPS, acts on monocytes, macrophages, granulocytes, and endothelial cells that express multiple genes encoding proinflammatory cytokines (TNFα, IL-1, 6, 8, and 12), signal transducers (iNOS and COX2), cell adhesion molecules (E-selectin, VCAM, ICAM) and procoagulant molecules (Tissue Factor, Plasminogen Activator Inhibitor).[48,49,67,68] Persistent expression of stress-responsive gene products changes the quiescent phenotype of blood cells and vascular endothelium into an "activated" phenotype and contributes to irreversible vascular dysfunction and leads to the ultimately fatal outcome.[47,49] NF-κB is a primary intracellular mediator of signaling to the nucleus induced by LPS in humans and mice wherein persistent nuclear translocation of NF-κB correlated with lethal outcome.[49] Unlike extracellular LPS inhibitors or cytokine receptor antagonists, the SN50 peptide blocks the pre-final obligatory step in intracellular signaling to the nucleus by NF-κB and other stress-responsive transactivators, regardless of the initiating stimulus.[50,52]

The in vivo mechanism of protective action of the SN50 peptide can be deduced from these studies. First, the SN50 peptide is likely to attenuate NF-κB-dependent expression of cytokines and other stress-responsive gene products contributing to cellular and molecular pathogenesis of septic shock. The inhibitory effect of the SN50 peptide on expression of genes regulated by NF-κB and other transactivators was demonstrated.[52] Second, it is unlikely that the primary cellular site of action of the SN50 peptide are LPS-stimulated peritoneal macrophages because they do not appear to be the major cells responsible for the overall host response during endotoxic shock.[69] Rather, we have proven that the SN50 peptide exerts its protective effect systemically being absorbed from peritoneal cavity and crossing plasma membrane of vascular endothelial cells as well as of blood monocytes and tissue macrophages. Therein, it reaches its intracellular target, importin −α and −β heterodimer (also called karyopherin −α and −β) shuttling NF-κB, AP-1, NFAT and STAT1 to the nucleus.[52] Significant cytoprotective effect in the liver and overall gain in survival following repeated intraperitoneal administration of the SN50 peptide indicate its systemic in vivo effect. Third, the observed in vivo cytoprotective effect of the SN50 peptide in the liver is remarkable in the context of the reported Janus-like role of NF-κB in preventing and inducing apoptosis.[63] Time-dependent anti-apoptotic effect of the SN50 peptide in the liver indicates that LPS and proinflammatory cytokine mediators, eg. TNFα and interferon γ, cannot induce apoptosis when nuclear import of NF-κB, AP-1, NFAT and STAT-1 is blocked by the SN50 peptide as previously demonstrated.[52] Other studies using genetically-engineered mice have provided significant insight in molecular mechanism of LPS-induced septic shock by pinpointing LPS receptors, cytokine receptors, and intracellular caspases as essential molecular mediators of septic shock.[54-59,70-73]

Methods

Animals and Treatment

C57BL/6 mice were obtained from the Jackson Laboratory. 10–12 wk old female mice were injected intraperitoneally with 0.2 ml suspension of LPS from E. coli 0127:B8 (prepared by phenol extraction and gel filtration chromatography, Sigma Chemical Co.). D-galactosamine (20 mg in 0.2 ml; Sigma Chemical Co.) was injected intraperitoneally 30 minutes before LPS. Cell permeable SN50 and SM peptides (2 mg each in 0.2 ml) or 0.9% saline (diluent) were injected 30 min before and 30, 90, 150, 210 min after LPS. Additional intraperitoneal injections of the SN50 peptide to the survivors were administered 6 and 12 h after LPS. All injected agents were sterile and prepared in pyrogen-free saline for injections. Animals were observed at 2 h intervals during the first 12 h, at 4 h intervals during the subsequent 12 h and twice daily thereafter. Tissue sections from the liver, spleen, lungs, and kidneys were examined. Mice receiving either D-galactosamine (20 mg) alone (n=5) or LPS (1 μg) alone (n=5) survived and were unaffected on the basis of tissue sections from the principal organs. Animals were handled and experimental procedures were conducted in accordance with the American Association of Accreditation of Laboratory Animal Care guidelines and approved by the Institutional Animal Care Committee.

Cell-permeable Peptides

The SN50 and SM peptides were synthesized, filter-sterilized, and analyzed as described.[51,52]

Cell Cultures

Murine macrophage RAW 264.7 cell line obtained from the American Type Culture Collection (Rockville, Md.) and murine endothelial (LEII) cells obtained from Dr. T. Maciag (Maine Medical Center, Portland, Me.) were cultured in Dulbecco Minimal Essential Medium supplemented with 10% heat-inactivated fetal bovine serum containing no detectable LPS (<0.006 ng/ml as determined by the manufacturer, Atlanta Biological, Norcross, Ga.), 2 mM L-glutamine and antibiotics as recommended by ATCC. Where indicated, 5 ml of RAW 264.7 or LEII cells ($10^6$/ml) were stimulated with LPS from Escherichia coli 0127:B8 (Difco) or TNFα with the potency of 32,000 U per μg (Mallinckrodt) at concentrations and tissue indicated in the text.

Electrophoretic Mobility Gel Shift Assay (EMSA)

To measure nuclear import of NF-κB in RAW 264.7 and LEII cells, EMSA was performed as described using a radiolabeled κB probe.[51,52]

Statistical Analysis

The log rank test was used to determine P values for mouse survival data.[61]

EXAMPLE III

Figure 3A:
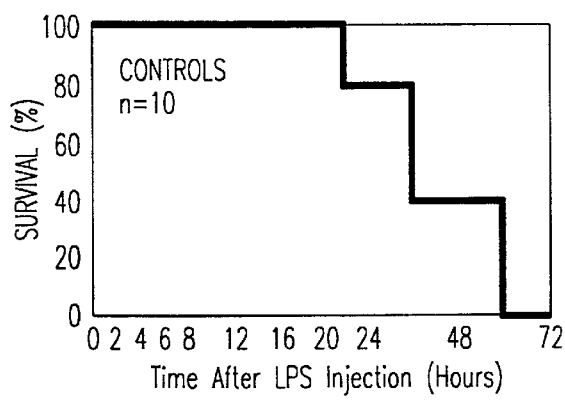
FIGS. 3A–3E illustrate the survival of mice after LPS. Female C57B1/6 mice(20 g) were randomly grouped (5 mice per group) and received intraperitoneal injections of LPS (*E. coli* 0127:B5, 800 μg). Treatments included cSN50 (1.5 mg or 0.7 mg) and SM peptide (1.5 mg) given 30 min before LPS, and afterwards at 30,90,150, 210 minutes and 6 hrs and 12 hrs.
Figure 3B:
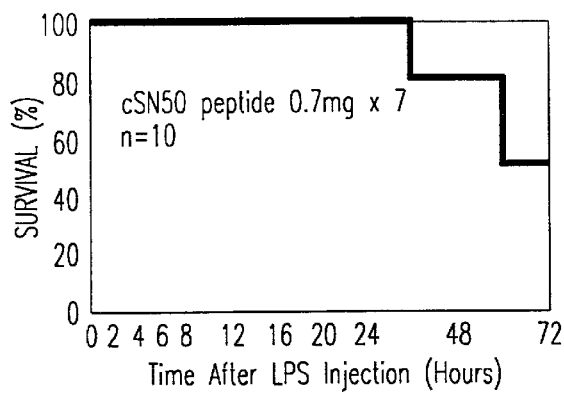
Figure 3C:
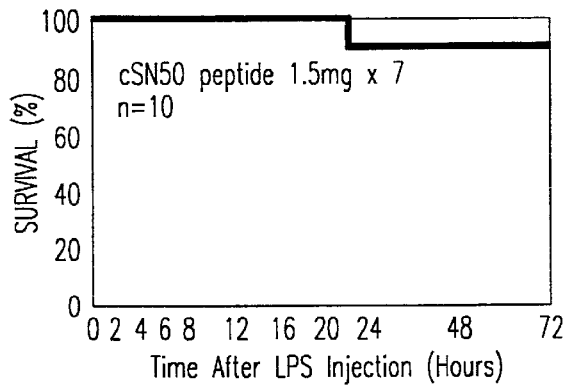
Figure 3D:
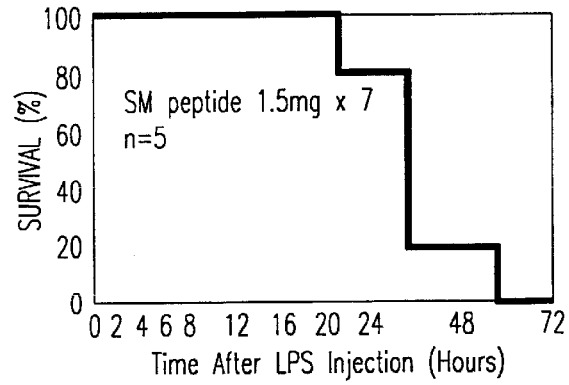
Figure 3E:
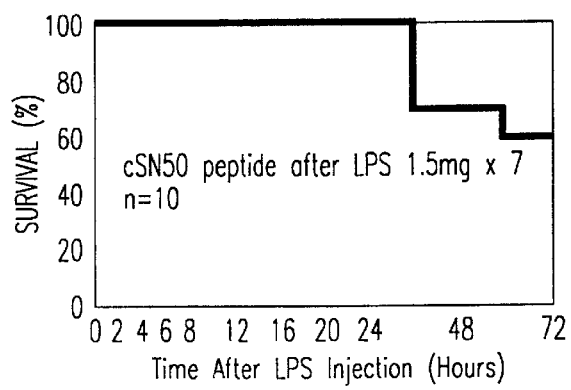

In this experiment, the effectiveness of this class of cell-permeable peptides in vitro with murine macrophages and endothelial cells was measured using SN50, carrying a nuclear localization sequence (NLS) derived from NF-κB1 (p50), SM, were synthesized and purified as previously described,[51,52] and a third cyclic peptide (cSN50) was designed by inserting two cysteines flanking NLS motif to form an intrachain disulfide bond. (cSN50 peptide, listed herein as SEQ ID NO: 12) All three peptides are cell-permeable, but the SM peptide functional domain contains a mutated NLS that is not recognized by importin α (also called karyopherin α or Rch 1).[52] In murine J774 macrophages, nuclear import of NF-κB in response to LPS (10 ng/ml) was blocked by SN50 but not SM (both at 100 μM). Similar results were obtained when J774 cells were stimulated with TNFα (20 U/ml), a proinflammatory mediator of septic shock. The SN50 peptide also inhibited inducible nuclear import of NF-κB in murine endothelial LEII cells stimulated with LPS (10 ng/ml) and TNFα (20 U/ml). The third peptide, cSN50 containing a cyclized NLS domain, was inhibitory at a concentration of 10 to 30 μM. Based on quantitative phosphoimager analysis of these results, the potency of cSN50 is 3–10 times greater than the prototypical SN50 peptide. Thus, cell-permeable peptides inhibited nuclear import of SRTFs in endotoxin-responsive cells in vitro.

cSN50 was tested in vivo using a murine model for lethal endotoxic shock.[60] In this model, LPS from *E. coli* serotype 0127:B8 ($LD_{100}$=800 μg) was injected intraperitoneally into C57BL/6 mice. As shown in FIG. 3A, all animals died within 72 hrs following LPS injection. In contrast, mice treated with cSN50 (0.7 mg given in 7 injections 30 minutes before to 12 hrs after LPS challenge) were protected from septic shock as evidenced by the lack of its typical signs (piloerection, lethargy, diarrhea, hemorrhagic conjunctivitis, hemorrhagic skin necrosis, and paralysis). During subsequent 24 hrs 1 animal died and after 48 hrs 4 died, yielding a 50% survival rate (FIG. 3B). The protective effect of cSN50 was improved when the dose was increased to 1.5 mg per injection (FIG. 3C). All but one animal survived for 72 hrs (90% survival). Survivors observed for the subsequent 10 days showed no apparent signs of disease. This in vivo protective effect was lost if the functional NLS motif was mutated as in the SM peptide. All SM peptide-treated mice died within 72 hrs (FIG. 3D). Based on the log rank test, the difference in survival rate between cSN50 peptide-treated groups and controls was statistically significant ($p<0.001$). Histologic examination of excised organs (lungs, liver, spleen, and kidneys) showed minimal changes in cSN50 peptide-treated survivors whereas untreated mice dying from endotoxin showed particularly prominent distention and engorgement of pulmonary vessels.

Prior studies have shown that following injection of LPS into humans and animals there is an early burst of proinflammatory cytokine mediators of septic shock such as TNFα, IL-1, and INF-γ.(75) To determine whether the cSN50 peptide reduces lethality when administered after exposure to endotoxin, the first peptide dose was given 30 min after endotoxin. The survival rate was 60%, indicating that the cSN50 peptide may exert its protective effect, if given shortly after exposure to endotoxin. Taken together, cSN50 peptide protected mice from endotoxin-induced lethal shock in a time and concentration-dependent manner. Increasing the dose of injected peptide and/or number of injections improved survival rate. The requirement for repeated administration of cell-permeable peptide indicates that its protective effect is transient; reducing the number of injections lowers the survival rate consistent with a relatively short intracellular half-time (~45 min) of SN50.[50] Thus, the rapidly reversible effect of cell-permeable peptide accounts for its short-term effectiveness and safety. No lethality or tissue injury was observed in animals receiving peptide alone.

The efficacy of the cell-permeable peptide described in this study likely reflects in vivo inhibition of signaling to the nucleus mediated by SRTFs.[51,52] In the absence of nuclear import inhibitor, SRTFs potently stimulate transcription of the genes encoding pro-inflammatory mediators of lethal shock.[48,68,77] In turn, the persistent expression of these genes in monocytes, macrophages, granulocytes, and endothelial cells is associated with profound vascular dysfunction and death.[48,49,57,68,77] The inhibitory effect of the SN50 peptide on the expression of genes regulated by NF-κB and other SRTF has been demonstrated.[52] The finding that the cell-permeable peptides carrying NLS inhibit nuclear import in vitro shows that they can prevent LPS-induced activation of these inflammatory stress-responsive genes in vivo. Consistent with this, mutations that inactivate NLS function yield a cell-permeable peptide (SM) that fails to affect the acute systemic inflammatory response to endotoxin.

These experiments provide a conceptually novel approach to treatment of endotoxic shock. In contrast to extracellular inhibitors of LPS or cytokine receptor antagonists,[75] nuclear import inhibitors of SRTFs are targeted intracellularly.[50] The multiple proinflammatory agonists, eg LPS and cytokines, upon binding to their cognate receptors, initiate a cascade of signaling steps converging at the common step of nuclear import of SRTFs.[48,54-58,68,77] Reversible inhibitors of nuclear import exemplified by cSN50 constitute a new class of anti-inflammatory agents capable of suppressing a systemic inflammatory response. Consistent with this approach, the SN50 peptide was effective in blocking lethal shock induced by superantigen, staphylococcal enterotoxin B, interacting with murine T lymphocytes.[76] In conclusion, our results with the NLS peptide functioning as nuclear import inhibitor provide a new, effective, and convenient in vivo targeting strategy to reduce morbidity and mortality in the systemic inflammatory response syndrome exemplified by endotoxic shock.

Methods

Animals and Treatment

C57BL/6 mice were obtained from the Jackson Laboratory. 8–12 wk old female mice (20 g weight) were injected intraperitoneally with 0.2 ml suspension of LPS (800 μg) from *E. coli* 0127:B8 (Difco, Detroit, Mich.). Cell-permeable cSN50 and SM peptides or 0.8% saline (diluent) were injected 30 min before and 30, 90, 150, 210 min, 6 hrs and 12 hrs after LPS. In some experiments cSN50 peptide was not injected before LPS. All injected agents were sterile and prepared in pyrogen-free saline. Animals were observed at 2 h intervals during the first 8 h, at 4 h intervals during the subsequent 16 h, and twice daily thereafter. Autopsies were performed shortly after death or after sacrifice at 72 hours. Surviving animals were observed for 10 days. Animals were handled and experimental procedures were conducted in accordance with the American Association of Accreditation of Laboratory Animal Care guidelines and approved by the Institutional Animal Care Committee.

Cell-permeable Peptides

The SN50 and SM peptides were synthesized, filter-sterilized, and analyzed as described.[11,12,51,52] The cSN50 peptide was synthesized and analyzed in a similar manner.

Cell Cultures

Murine macrophage J774 cell line was obtained from the American Type Culture Collection (Rockville, Md.) and murine endothelial (LEII) cells were kindly provided by Dr. T. Maciag (Maine Medical Center, Portland, Me). Both cell lines were cultured in Dulbecco Minimal Essential Medium supplemented with 10% heat-inactivated fetal bovine serum containing no detectable LPS (<0.006 ng/ml as determined by the manufacturer, Atlanta Biological, Norcross, Ga.), 2 mM L-glutamine and antibiotics. Where indicated, 80% confluent monolayers of J774 or 100% confluent LEII cells (100 mm plates with 10 ml fresh medium) were stimulated with LPS from *Escherichia coli* 0127:B8 (Difco) or with TNFα (32,000 U per μg; Mallinckrodt) at concentrations and time indicated in the text. Nuclear import of NF-κB in J774 and LEII cells was measured by Electrophoretic mobility gel shift assay (EMSA) using a radiolabeled κB probe.[6,7]

Electrophoretic Mobility Gel Shift Assay (EMSA)

Measurement of the nuclear import of NF-κB was performed as described using a radiolabeled κB probe.[51,52]

Histologic Analysis

Formalin-fixed, paraffin-embedded sections of the liver, spleen, lungs, and kidneys were stained with hematoxylin and eosin to assess overall histology.

Statistical Analysis

The log rank test was used to determine P values for mouse survival data.[61]

At the molecular level, systemic inflammatory response syndromes such as endotoxic shock are mediated via nuclear signaling of NF-κB and other stress-responsive transcription factors (SRTFs), which regulate the expression of septic shock mediators.[48,49] These findings demonstrate the in vivo utility of cell-permeating peptide inhibitor of NF-κB in the therapeutic control of an acute systemic inflammatory response at the level of nuclear signaling. Inhibition of nuclear import of SRTFs with a cyclic cell-permeable peptide demonstrates a new approach to the control of systemic inflammatory response syndromes such as endotoxic shock.

Septic shock triggered by endotoxic lipopolysaccharide (LPS) is an extreme form of the systemic inflammatory response syndrome that is characterized by collapse of the circulatory system, disseminated intravascular coagulation, and multiple organ failure resulting in high morbidity and mortality.[46,47] Treatment of septic shock is often ineffectual, as diverse mediators lead to fatal outcome.[53,66] These mediators are expressed because SRTFs relay signals to the nuclei in endotoxin-responsive cells (monocytes, macrophages, endothelial cells).[48,68,77]

There is abundant evidence that SRTFs, reaching the nuclei from the cytoplasm, activate genes encoding proinflammatory cytokines such as, tumor necrosis factor α (TNFα), interleukins 1,6,8,12,18, cell adhesion molecules, ICAM-1, E selectin and VCAM, as well as the procoagulant molecules, tissue factor and plasminogen activator inhibitor.[48,68,77] The SRTFs, mediating responses to inflammatory and immune stress are NF-κB, AP-1, NFAT and STAT-1.[48,49,57,67,68,77] For example, NF-κB and NFAT regulate genes encoding primary cytokine mediators of septic shock, TNFα and interferon γ (INF-γ).[74] The gene encoding tissue factor, a primary procoagulant mediator of disseminated intravascular coagulation, is regulated by NF-κB and AP1.[68]

In humans and mice, persistent nuclear translocation of NF-κB in mononuclear phagocytic cells correlated with lethal outcome of septic shock.[49] Nuclear import of these transactivators can be blocked by non-invasive intracellular delivery of SN50 peptide bearing a membrane translocation motif and a functional domain comprised of the nuclear localization sequence (NLS) derived from NF-κB and recognized by heterodimer of importin α and importin β (also called karyopherin –α and –β).[50-52] These in vivo findings present a novel approach to the therapeutic control of lethal septic shock involving the delivery of cell-permeable peptides that affect nuclear targeting of NF-κB and other stress-responsive transactivators.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

REFERENCES 1. von Heijne, *J. Membrane Biol* 115:195–201 (1990).
2. Rapoport, *Science* 258:931–936 (1992).
3. Gilmore, *Cell* 75:589–592 (1993).
4. Sanders and Schekman, *J Bio. Chem* 267:13791–13794 (1992).
5. Nunnari and Walter, *Curr. Opin. Cell Biol.* 4:573–580 (1992).
6. Simon and Blobel, *Cell* 65:371–380 (1991).
7. Poritz et al., *Science* 250:1111–1117 (1990).
8. Ribes et al, *Cell* 63:591–600 (1990).
9. Luirink et al., *Nature* 359:741–743 (1992).
10. Phillips and Sihavy, *Nature* 359:744–746 (1992).
11. Simon and Blobel, *Cell* 69:677–684 (1992).
12. Cobet et al., *J. Biol. Chem.* 264:1016 9–10176 (1989).
13. Zimmermann, et al., *Biochimie* 72:95–101 (1990).
14. Wickner, *Biochemistry* 27:1081–1086 (1988).
15. Killian et al., *EMBO J.* 9:815–819 (1990).
16. Delli Bovi et al., *Cell* 50:729–737 (1987).
17. Taira et al., *Proc. Natl Acad. Sci. U.S.A.* 84:2980–2984 (1987).
18. Imamura et al., *Science* 249:1567–1570 (1990).
19. Imamura and Mitsui, *J. Biol Chem* 267:5676–5679 (1992).
20. Kajstura. and Reiss, *K Folia Histochem. Cytobiol.* 27:39–48 (1989).
21. Kimura, *Proc. Natl. Acad, Sci USA* 90:2165–2169 (1993).
22. Coughlin et al., *J. Biol. Chem.* 263:988–993 (1988).
23. Friesel et al, *Molec. Cell. Biol.* 9:1857–1865 (1989).
24. Merrifield, *J. Am Chem. Soc.* 85:2149–2154 (1963).
25. Lin et al. *Biochemistry* 27:5640–5645 (1988).
26. *Physician's Desk Reference,* 47th Ed., Medical Economics Data, Montvale, N.J., p. 2555 (1993).
27. *Remington's Pharmaceutical Sciences,* 18th Ed., E. W. Martin (ed.), Mack Publishing Co., Easton, Pa. (1990).
28. Sambrook et al., *Molecular Cloning: A Laboratory Manual,* 2nd Ed., Cold Spring Harbor Laboratory, Cold Spring Harbor, N.Y. (1989).
29. Walter et al. *Proc. Natl. Acad. Sci. USA* 77:5197 (1980).
30. von Heijne, *Protein Sequence Data Analysis* Vol. 1:41–42 (19.87).
31. Goodfriend et al. *Science* 143:1344 (1964).
32. Hawley-Nelson et al. *Focus* 15(3):73–83 (1992).
33. FeIgner et al. *Proc. Natl. Acad. Sci. U.S.A.* 84:7413 (1987).
34. Stewart et al. *Human Gene Therapy* 3:267–275 (1992).
35. Nicolau et al. *Methods Enzymol.* 149:157 (1987).
36. Adam, S. A, et al. *Nature* 337:276–279 (1989).
37. Goldfarb, D. S. et al. *Nature* 322:641–644 (1986).
38. von Heijne and Abrahmsen, L., *FEBS Letters* 224:439–446 (1989).
39. Lenardo, M J. and Baltimore, D., *Cell* 58:227 (1989).
40. Baeuerle, P A,. and Baltimore, D., *Mol. Aspects Cell. Regul.* 6:409 (1991).
41. Baeuerle, P A and Baltimore, D., *Cell* 53:211 (1988).
42. Baeuerle, P. A. and Baltimore, D., *Science* 242:540 (1988).
43. Cordle, S. R. et al. *J Biol. Chem* 268:11803 (1993).
44. Sen, R. and Baltimore, D., *Cell* 46:705 (1986).
45. Liberman, T. A. and Baltimore, D., *Mol Cell. Biol.* 10:2327 (1990).
46. Increase in national hospital discharge survey rates for septicemia: United States, 1979–1987. MMWR 39, 31–34 (1990).
47. Glauser, M. P., Zanetti, G., Baumgartner, J. D., and Cohen. J. Septic shock: pathogenesis Lancet 338, 732–6 (1991).
48. Baldwin, A. S., The NF-κB and I-κB proteins: new discoveries and insights. Annu. Rev. Immunol. 14, 649–81 (1996).
49. Bohrer, H., et al. Role of NF-κB in the mortality of sepsis. J Clin Invest 100, 972–85 (1997).
50. Hawiger, J. Noninvasive intracellular delivery of functional peptides and proteins. Curr. Opin. Chem. Biol. 3, 89–94 (1999).

51. Lin, Y. Z., Yao, S. Y., Veach, R. A., Torgerson, T. R., and Hawiger, J. Inhibition of nuclear translocation of transcription factor NF-kappa B by a synthetic peptide containing a cell membrane-permeable motif and nuclear localization sequence. J. of Biol. Chem. 270,14255–8 (1995).
52. Torgerson, T. R., Colosia, A. D., Donahue, J. P., Lin, Y. Z., Hawiger, J. Regulation of NF-kappa B, AP-1, NFAT, and STAT1 nuclear import in T lymphocytes by noninvasive delivery of peptide carrying the nuclear localization sequence of NF-kappa B. J. Immunol. 161, 6084–92 (1998).
53. Baumgartner, J. D. and Calandra, T. Treatement of Sepsis: Past and Future Avenues. Drugs 57,127–132 (1999).
54. Haziot A., Ferrero E., Kontgen F., Hijiya N., Yamamoto S., et al. Resistance to endotoxin shock and reduced dissemination of gram-negative bacteria in CD14-deficient mice. Immunity 4, 407–14 (1996).
55. Poltorak A., He X., Smirnova I., Liu M. Y., Huffel C. V. Defective LPS signaling in C3H/HeJ and C57BL/10ScCr mice: mutations in Tlr4 gene. Science 282, 2085–8 (1998).
56. Rothe J., Lesslauer W., Lotscher H., Lang Y., Koebel P., et al. Mice lacking the tumor necrosis factor receptor 1 are resistant to TNF-mediated toxicity but highly susceptible to infection by Listeria monocytogenes. Nature 26, 798–802 (1993).
57. Car, B. D,. Eng, V. M., Schnyder, B., Ozmen, L., Huang, S., et al. Interferon γ Receptor Deficient Mice are Resistant to Endotoxic Shock. J Exp. Med. 179,1437–44 (1994).
58. Li, P., Allen, H., Banerjee, S., Franklin, S., Herzog, L., et al. Mice Deficient In IL-1 β-converting Enzyme Are Defective In Production of Mature IL-1 and Resistant to Endotoxic Shock. Cell 80, 401–411 (1995).
59. Fantuzzi, G. and Dinarello, C. A., The Inflammatory Response in Interleukin-1β-Deficient Mice: Comparison with Other Cytokine-Related Knock-Out Mice. J. Leukocyte Biology 59, 489 (1996).
60. Galanos, C., Freudenberg, M. A., Reutter, W., Galactosamine-induced sensitization to the lethal effects of endotoxin. Proc. Natl. Acad. Sci. USA 76,5939–5943 (1979).
61. Dawson-Saunder, B., Trapp, R. G., Basic and Clinical Biostatistics. 2nd Edition (Appleton & Lange, Norwalk, Conn. 1994).
62. Morikawa, A., Sugiyama, T., Kato, Y., Koide, N., Jiang, G Z., Apoptotic cell death in the response of D-galactosamine-sensitized mice to lipopolysaccharide as an experimental endotoxic shock model. Infect. Immun. 64,734–8 (1996).
63. Baichwal, V. R. & Baeuerle, P. A. Apoptosis: Activate NF-κB or die? Curr. Biol. 7, R94–96 (1997).
64. Beg, A. A., Sha, W. C., Bronson, R. T., Ghosh, S., Baltimore, D. Embryonic lethality and liver degeneration in mice lacking the Re1A component of NF-κB. Nature 376:167–70 (1995).
65. Li, Q. Antwerp, D. V., Mercurio, F., Lee, K. F., Verma, I. M., Severe Liver Degeneration in Mice Lacking the IκB Kinase 2 Gene. Science 284:321–25 (1999).
66. Natanson, C., Hoffman, W. D., Suffredini, A. F., Eichacker, P. Q., and Danner, R. L. Selected treatment strategies for septic shock based on proposed mechanism of pathogenesis. Ann. Intern. Med. 120, 771–787 (1994).
67. Hawiger, J., Lipopolysaccharide-induced signal transduction and gene transcription, in Endotoxin and the lungs, K. L. Brigham, Editor. 69–82 (Marcel Dekker, Inc. New York., 1994).
68. Mackman, N. Regulation of the tissue factor gene. FASEB J. 9, 883–889 (1995).
69. Amura, C. R., Silverstein, R., Morrison, D. C. Mechanisms involved in the pathogenesis of sepsis are not necessarily reflected by in vitro cell activation studies. Infect Immun 66, 5372–8 (1998).
70. Jack, R. S., Fan, X., Bernheiden, M., Rune, G., Ehlers, M. Lipopolysaccharide-binding protein is required to combat a murine gram-negative bacterial infection. Nature 389, 742–5 (1997).
71. Pfeffer K., Matsuyama T., Kundig T. M., Wakeham A., Kishihara K., et al. Mice deficient for the 55 kd tumor necrosis factor receptor are resistant to endotoxic shock, yet succumb to L. monocytogenes infection. Cell 7, 457–67 (1993).
72. Erickson S. L., de Sauvage F. J., Kikly K., Carver-Moore K., Pitts-Meek S. Decreased sensitivity to tumor-necrosis factor but normal T-cell development in TNF receptor-2-deficient mice. Nature 8, 560–3 (1994).
73. Wang, S., Miura, M., Jung, Y. K., Zhu, H., Li, E., et al. Murine caspase-11, an ICE-interacting protease, is essential for the activation of ICE. Cell 20, 501–9 (1998).
74. A. E. Goldfeld, P. G. McCaffrey, J. L. Strominger, A. Rao. J. Exp. Med. 178, 1365 (1993); A. Sica, et al. J. Biol. Chem. 272, 30412 (1997).
75. K. J. Tracey, et al Nature 330, 662 (1987); H. R. Michie, et al. N. Engl. J. Med. 318, 1481 (1988); D. G. Hesse, et al. Surg. Gynecol. Obstet. 166, 147 (1988); R.P. et al. Ann. Surg. 210, 239 (1989); D. G. Remick, et al. Am. J. Path. 136, 49 (1990); H. R. Alexander, G. M. Doherty, C. M. Buresh, D. J. Venzon, J. A. Norton. J. Exp. Med. 173, 1029 (1991).
76. J. Hawiger, D. Robinson, L. Seele, R. A. Veach, X. Y. Liu, S. Timmons, R. D. Collins, D. W. Ballard (unpublished observations).
77. J. Hawiger, in Endotoxin and the Lungs; K. Brigham, Ed. (Marcel Dekker, Inc., New York, Basel, Hong Kong, 1994) pp. 69–82.

What is claimed is:

1. A method of importing a nuclear localization sequence of NF-κB into a cell in a subject, comprising administering a cyclic peptide consisting essentially of SEQ ID NO: 12 to the subject, wherein said cyclic peptide is imported into a cell in the subject.

* * * * *

SEQUENCE LISTING

<160> NUMBER OF SEQ ID NOS: 13

<210> SEQ ID NO 1
<211> LENGTH: 26
<212> TYPE: PRT
<213> ORGANISM: Artificial Sequence
<220> FEATURE:

<223> OTHER INFORMATION: 1..16 Note:/label = a ("Signal peptide amino
      acid sequence of K-FGF")
<223> OTHER INFORMATION: 17..19 Note:/label = b ("Spacer region")
<223> OTHER INFORMATION: 20..26 Note:/label = c ("Epitope tag")
<223> OTHER INFORMATION: Description of Artificial Sequence:/Note =
      synthetic construct

<400> SEQUENCE: 1

Ala Ala Val Ala Leu Leu Pro Ala Val Leu Leu Ala Leu Leu Ala Pro
 1               5                  10                  15

Ala Ala Ala Asp Gln Asn Gln Leu Met Pro
            20                  25

<210> SEQ ID NO 2
<211> LENGTH: 7
<212> TYPE: PRT
<213> ORGANISM: Artificial Sequence
<220> FEATURE:
<223> OTHER INFORMATION: 1..7 Note:/label = a ("Nuclear localization
      sequence of aFGF")
<223> OTHER INFORMATION: Description of Artificial Sequence:/Note =
      synthetic construct

<400> SEQUENCE: 2

Asn Tyr Lys Lys Pro Lys Leu
 1               5

<210> SEQ ID NO 3
<211> LENGTH: 26
<212> TYPE: PRT
<213> ORGANISM: Artificial Sequence
<220> FEATURE:
<223> OTHER INFORMATION: 1..16 Note:/label = a ("Signal peptide amino
      acid sequence of K-FGF")
<223> OTHER INFORMATION: 17..19 Note:/label = b ("Spacer region")
<223> OTHER INFORMATION: 20..26 Note:/label = c ("Nuclear localization
      sequence of aFGF")
<223> OTHER INFORMATION: Description of Artificial Sequence:/Note =
      synthetic construct

<400> SEQUENCE: 3

Ala Ala Val Ala Leu Leu Pro Ala Val Leu Leu Ala Leu Leu Ala Pro
 1               5                  10                  15

Ala Ala Ala Asn Tyr Lys Lys Pro Lys Leu
            20                  25

<210> SEQ ID NO 4
<211> LENGTH: 28
<212> TYPE: PRT
<213> ORGANISM: Artificial Sequence
<220> FEATURE:
<223> OTHER INFORMATION: 1..16 Note:/label = a ("Signal peptide amino
      acid sequence of K-FGF")
<223> OTHER INFORMATION: 17..19 Note:/label = b ("Spacer region")
<223> OTHER INFORMATION: 20..26 Note:/label = c ("Nuclear localization
      sequence of aFGF")
<223> OTHER INFORMATION: 26..28 Note:/label = d ("Epitope tag)
<223> OTHER INFORMATION: Description of Artificial Sequence:/Note =
      synthetic construct

<400> SEQUENCE: 4

Ala Ala Val Ala Leu Leu Pro Ala Val Leu Leu Ala Leu Leu Ala Pro
 1               5                  10                  15

Ala Ala Ala Asn Tyr Lys Lys Pro Lys Leu Met Pro
            20                  25

<210> SEQ ID NO 5
<211> LENGTH: 16

```
<212> TYPE: PRT
<213> ORGANISM: Artificial Sequence
<220> FEATURE:
<223> OTHER INFORMATION: 1..16 Note:/label = a ("Signal peptide of
      K-FGF")
<223> OTHER INFORMATION: Description of Artificial Sequence:/Note =
      synthetic construct

<400> SEQUENCE: 5

Ala Ala Val Ala Leu Leu Pro Ala Val Leu Leu Ala Leu Leu Ala Pro
 1               5                  10                  15

<210> SEQ ID NO 6
<211> LENGTH: 41
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 6

Ala Ala Val Ala Leu Leu Pro Ala Val Leu Leu Ala Leu Leu Ala Pro
 1               5                  10                  15

Glu Ile Leu Leu Pro Asn Asn Tyr Asn Ala Tyr Glu Ser Tyr Lys Tyr
                20                  25                  30

Pro Gly Met Phe Ile Ala Leu Ser Lys
            35                  40

<210> SEQ ID NO 7
<211> LENGTH: 25
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 7

Glu Ile Leu Leu Pro Asn Asn Tyr Asn Ala Tyr Glu Ser Tyr Lys Tyr
 1               5                  10                  15

Pro Gly Met Phe Ile Ala Leu Ser Lys
                20                  25

<210> SEQ ID NO 8
<211> LENGTH: 26
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 8

Ala Ala Val Ala Leu Leu Pro Ala Val Leu Leu Ala Leu Leu Ala Pro
 1               5                  10                  15

Ile Glu Glu Lys Arg Lys Arg Thr Tyr Glu
                20                  25

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 9

Ala Ala Val Ala Leu Leu Pro Ala Val Leu Leu Ala Leu Leu Ala Pro
```

−continued

```
                1               5              10              15
Val Asn Arg Lys Arg Asn Lys Leu Met Pro
                               20              25
```

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 10

```
Val Ala Ser Asn Arg Lys Arg Asn Lys Leu Met Pro
1               5                  10
```

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 11

```
Ile Glu Glu Lys Arg Lys Arg Thr Tyr Glu
1               5                  10
```

<210> SEQ ID NO 12
<211> LENGTH: 31
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 12

```
Ala Ala Val Ala Leu Ala Leu Leu Pro Ala Val Leu Ala Leu Leu
1               5                  10                 15
Ala Pro Cys Tyr Val Gln Arg Lys Arg Gln Lys Leu Met Pro Cys
                20                 25                 30
```

<210> SEQ ID NO 13
<211> LENGTH: 26
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 13

```
Ala Ala Val Ala Leu Leu Pro Ala Val Leu Leu Ala Leu Leu Ala Pro
1               5                  10                 15
Val Gln Arg Lys Arg Gln Lys Leu Met Pro
                20                 25
```